(12) United States Patent
Roh et al.

(10) Patent No.: US 11,497,436 B1
(45) Date of Patent: Nov. 15, 2022

(54) SYSTEMS, METHODS, AND BONE MAPPER DEVICES FOR REAL-TIME MAPPING AND ANALYSIS OF BONE TISSUE

(71) Applicant: IX Innovation LLC, Seattle, WA (US)

(72) Inventors: Jeffrey Roh, Seattle, WA (US); Justin Esterberg, Mesa, AZ (US); John Cronin, Jericho, VT (US); Seth Cronin, Essex Junction, VT (US); Michael John Baker, Georgia, VT (US)

(73) Assignee: IX Innovation LLC, Seattle, WA (US)

( * ) Notice: Subject to any disclaimer, the term of this patent is extended or adjusted under 35 U.S.C. 154(b) by 0 days.

(21) Appl. No.: 17/746,608

(22) Filed: May 17, 2022

(51) Int. Cl.
*A61B 5/00* (2006.01)

(52) U.S. Cl.
CPC .......... *A61B 5/4509* (2013.01); *A61B 5/0095* (2013.01); *A61B 5/7267* (2013.01)

(58) Field of Classification Search
CPC ... A61B 5/4509; A61B 5/0095; A61B 5/7267; A61B 5/7203; A61B 5/14542; A61B 5/14546
See application file for complete search history.

(56) References Cited

U.S. PATENT DOCUMENTS

| | | | | |
|---|---|---|---|---|
| 5,353,262 A | * | 10/1994 | Yakymyshyn | G01H 9/00 73/632 |
| 5,530,780 A | * | 6/1996 | Ohsawa | G02B 6/3624 385/901 |
| 8,454,512 B2 | * | 6/2013 | Wang | G01N 29/0681 600/459 |
| 9,662,020 B2 | * | 5/2017 | Irisawa | A61B 5/0095 |
| 9,730,587 B2 | * | 8/2017 | Herzog | G01N 29/30 |
| 9,743,881 B2 | * | 8/2017 | Radulescu | A61B 5/0095 |
| 9,949,717 B2 | * | 4/2018 | Rozental | A61B 8/44 |
| 10,531,828 B2 | * | 1/2020 | Bell | A61B 34/20 |
| 2002/0105250 A1 | * | 8/2002 | Klee | B06B 1/0622 310/365 |
| 2006/0238067 A1 | * | 10/2006 | Dausch | B06B 1/0622 310/311 |
| 2007/0206193 A1 | * | 9/2007 | Pesach | A61B 5/0095 356/432 |
| 2008/0004686 A1 | * | 1/2008 | Hunt | A61L 31/14 606/14 |

(Continued)

*Primary Examiner* — Sanjay Cattungal
(74) *Attorney, Agent, or Firm* — Perkins Coie LLP

(57) ABSTRACT

Apparatuses, systems, and methods for performing real-time analysis of bone tissue during a surgical procedure are disclosed herein. In some embodiments, the method includes receiving at least one measurement of at least one tissue sample from a hybrid multi-wavelength photoacoustic measurements (MWPM) component. The method can also include identifying one or more reference cases, from a plurality of reference cases, based on correlations between the at least one measurement and previous measurements in each of the plurality of reference cases. Once the reference cases are identified, the method can include determining at least one bone condition of the patient and sending the at least one determined bone condition to a computing device accessible by a surgeon. In some embodiments, the method also includes creating a three-dimensional (3D) map the tissue sample using the at least one measurement and sending the 3D map to the computing device.

20 Claims, 14 Drawing Sheets

(56) References Cited

U.S. PATENT DOCUMENTS

| | | | |
|---|---|---|---|
| 2008/0221647 A1* | 9/2008 | Chamberland | A61N 5/062 |
| | | | 382/131 |
| 2009/0002685 A1* | 1/2009 | Fukutani | A61B 5/0073 |
| | | | 181/141 |
| 2011/0201973 A1* | 8/2011 | Stephens | A61B 8/12 |
| | | | 601/2 |
| 2012/0275262 A1* | 11/2012 | Song | G01N 29/2418 |
| | | | 367/7 |
| 2013/0199299 A1* | 8/2013 | Wang | A61B 5/7257 |
| | | | 73/655 |
| 2014/0046165 A1* | 2/2014 | Fukutani | A61B 5/02007 |
| | | | 600/407 |
| 2014/0051967 A1* | 2/2014 | Irisawa | A61B 5/0095 |
| | | | 600/407 |
| 2014/0360273 A1* | 12/2014 | Zhang | G01N 29/14 |
| | | | 73/643 |
| 2014/0371571 A1* | 12/2014 | Tsujita | A61B 5/0095 |
| | | | 600/407 |
| 2015/0217142 A1* | 8/2015 | Schafer | A61N 5/0624 |
| | | | 601/2 |
| 2015/0245771 A1* | 9/2015 | Wang | A61B 5/725 |
| | | | 600/407 |
| 2015/0272444 A1* | 10/2015 | Maslov | A61B 5/0095 |
| | | | 703/2 |
| 2015/0359478 A1* | 12/2015 | Eyal | A61B 5/0095 |
| | | | 600/407 |
| 2017/0000353 A1* | 1/2017 | Li | A61B 1/0615 |
| 2021/0137602 A1* | 5/2021 | Goodwin | G16H 30/40 |

* cited by examiner

| OPERATING ROOM REAL-TIME EQUIPMENT DATABASE (DATE OF OPERATING 21-JUNE-2018, BY DR VAN) | | | | | | | |
|---|---|---|---|---|---|---|---|
| Patient | Time Interval | BMD Values | MWPM Value (nm) | Energy Per Laser Pulse (mJ/cm²) | µ3 Value | Photoacoustic (PA) Signal (laser pulses/second) | Parameters Detected From Imaging Device |
| Alex | 01:25:30 PM | 2.5 | 730 | 15 | 2 | 50 | High Dense Structure |
| | 01:25:35 PM | 1.9 | 780 | 15 | 2.5 | 50 | Porous Structure |
| | 01:25:40 PM | 2.0 | 705 | 15 | 3 | 50 | Less Dense Bone |
| | 01:25:40 PM | 1.5 | 710 | 15 | 2 | 50 | Highly Porous Structure |

| Patient Number | BMD Spectrum Readings | MWPM Value (Range Between 700-950) (nm) | Energy Per Laser Pulse Range (mJ/cm²) | µ3 Value | Imaging Device Diagnosis of Bone | Final Diagnosis of Bone |
|---|---|---|---|---|---|---|
| Patient 1 | 2.2 | 730 | 15 | 2 | High Dense Structure | Normal Bone |
|  | 1.8 | 790 | 20 | 2.5 | Porous Structure | Osteoporosis |
| Patient 2 | 2.0 | 705 | 16 | 3 | Less Dense Bond | Normal |
|  | 1.6 | 800 | 20 | 2 | Highly Porous Structure | Osteoporosis |

EXTERNAL REAL-TIME ANALYSIS BONE DATABASE

FIG. 12

| Patient Number | Previous Health Condition | Imaging Device Diagnosis | Final Diagnosis |
|---|---|---|---|
| Patient 1 | Diabetic | Brown Spots | Skin Cancer |
| Patient 2 | High Blood Pressure | Dark Brown Spots | Skin Cancer |

EXTERNAL REAL-TIME ANALYSIS PATHOLOGY DATABASE

*FIG. 13*

SYSTEMS, METHODS, AND BONE MAPPER DEVICES FOR REAL-TIME MAPPING AND ANALYSIS OF BONE TISSUE

TECHNICAL FIELD

The present disclosure is generally related to apparatuses, systems, and methods for surgical analysis of tissue samples and, more specifically, to bone mapper devices for real-time mapping and/or analysis of bone tissue using multi-wavelength photoacoustic measurements.

BACKGROUND

More than 200 million surgeries are performed worldwide each year, and recent reports reveal that adverse event rates for surgical conditions remain unacceptably high, despite traditional patient safety initiatives. Adverse events resulting from surgical interventions can be related to errors occurring before or after the procedure as well as technical surgical errors during the operation. For example, adverse events can occur due to (i) breakdown in communication within and among the surgical team, care providers, patients, and their families; (ii) delay in diagnosis or failure to diagnose; and (iii) delay in treatment or failure to treat. The risk of complications during surgery can include anesthesia complications, hemorrhaging, high blood pressure, a rise or fall in body temperature, etc. Such adverse events can further occur due to medical errors, infections, underlying physical or health conditions of the patient, reactions to anesthetics or other drugs, etc. Conventional methods for preventing wrong-site, wrong-person, wrong-procedure errors, or retained foreign objects are typically based on communication between the patient, the surgeon(s), and other members of the health care team. However, conventional methods are typically insufficient to prevent surgical errors and adverse events during surgery.

BRIEF DESCRIPTION OF THE DRAWINGS

FIG. 9 is a table illustrating an example operating room real-time equipment database in accordance with some embodiments of the present technology.

FIG. 12 is a table illustrating an example bone database in accordance with some embodiments of the present technology FIG. 13 is a table illustrating an example pathology database in accordance with some embodiments of the present technology The drawings have not necessarily been drawn to scale. Similarly, some components and/or operations can be separated into different blocks or combined into a single block for the purpose of discussion of some of the implementations of the present technology. Moreover, while the technology is amenable to various modifications and alternative forms, specific implementations have been shown by way of example in the drawings and are described in detail below. The intention, however, is not to limit the technology to the particular implementations described.

DETAILED DESCRIPTION

Overview

Figure 1:
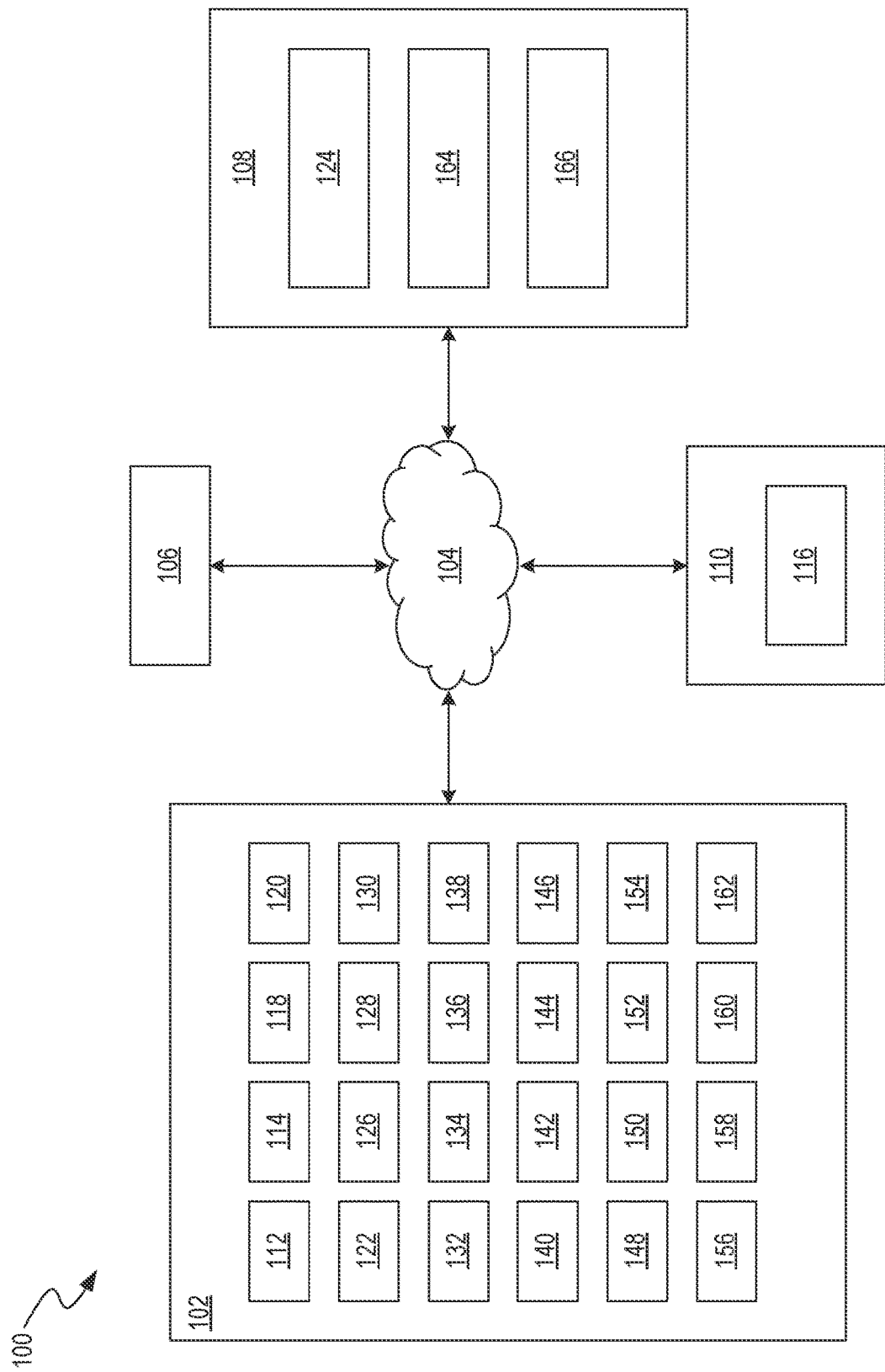
FIG. 1 is a block diagram illustrating an example surgical system, in accordance with one or more embodiments.

An individual's tissue composition and skeletal structures change throughout their life. For example, changes in bone masses and bone structures (sometimes referred to collectively as "bone mass" herein) are generally characterized by a period of growth (e.g., linear growth of endochondral growth plates and radial growth from periosteal apposition) and a period of slow loss as the individual ages. Loss of bone mass during the latter period can lead to and/or be accelerated by a variety of medical conditions. For example, osteoporosis is a debilitating disease characterized by large decreases in skeletal bone mass and mineral density, structural deterioration of bones (e.g., degradation of bone microarchitecture), and/or increases in bone fragility and susceptibility to fracture. Osteoporosis is often preceded by clinical osteopenia, which is a condition defined by a bone mineral density that is below the mean value for bone mineral density for an individual's age by between 1 and 2.5 standard deviations. Osteoporosis is one of the most expensive diseases to detect and treat, and is associated with long-term residential care and lost working days while an individual is treated. Early and accurate detection of changes to an individual's bone mass and structures, for example during clinical osteopenia, can drastically reduce the costs and lost time associated with treatment. However, osteopenia typically does not result in many physical symptoms of reducing bone density (e.g., pain, noticeable increases in bone fragility, and the like). Further, although there are a variety of techniques and chemical analyses available to calculate bone material density and detect changes in bone density, conventional detection techniques are often limited by cost, accessibility, and dangers associated with the detection techniques. As a result, it can be difficult to confirm that an individual has osteoporosis even when they are exhibiting physical symptoms, let alone anytime before then.

For example, conventional techniques for monitoring tissue composition and bone masses (e.g., to detect and monitor osteoporosis) often begin with a non-invasive assessment method based on the use of X-rays or ultrasound to measure an individual's bone mass density (BMD). But X-ray-based techniques use ionizing radiation, which is not ideal for pediatric and/or long-term, repetitive monitoring of an individual's bone mass. Dual-energy X-ray absorptiometry (DEXA) is a related technique that uses two low-dosage X-ray beams to measure BMD. In a DEXA technique, X-ray beams with differing energy levels are aimed at the patient's spine, hip, or whole body to take measurements. A computer can then calculate the individual's BMD based on the fact that different bones and/or bone densities absorb different energy levels. DEXA techniques can be highly accurate, but they involve complex equipment that is bulky, expensive, and still require exposure to radiation. Furthermore, both X-rays and DEXA are limited by their operating wavelength and are typically unable to detect important details about the microstructure of a bone, organic matrixes associated with the individual's bone, and the like.

Quantitative ultrasound (QUS) technology is another example that is a relatively low-cost alternative compared to the X-ray-based techniques. Because QUS methods are primarily based on the measurement of sound velocity and broadband ultrasound attenuation through tissue, the QUS methods avoid exposure to radiation. However, the specificity of identifying bone composition in QUS methods is limited when bone diseases are determined by microstructure and chemical changes in the bone. This limitation is significant because an individual's bone health is dependent on not only the mass and structure of non-organic mineral matrixes but also the organic matrixes associated with the individual's bone blood flow and cellular metabolism. Furthermore, the QUS methods require a long turnaround time to provide a complete analysis of the tissue or a biopsy sample.

The use of biochemical sensors is another option to help monitor bone mass. Biochemical sensors can provide real-time information from in situ measurements. However, safely incorporating biosensors, such as acoustic emission sensors, in monitoring bone masses requires careful surgical implantation and coupling of the sensors. For example, incorrect sensor placement can result in damage to the bone masses sought to be monitored. Further, surgical implantation can lead to infections and other adverse surgical-related complications. Additionally, the materials necessary for biosensors are often expensive and/or restricted by public health agencies.

Optical imaging of tissue is yet another option for monitoring bone mass. For example, conventional multi-wavelength photoacoustic measurements (MWPM) generate a μ3 value that can be used to monitor and assess an individual's bone density and changes over time (sometimes also referred to as multi-wavelength photoacoustic (MWPA) analysis). However, tissue is a highly scattering medium for electromagnetic waves in the optical spectral range that imposes limits on the use of optical imaging techniques. As a result, two optical imaging techniques have been developed. Ballistic (minimally scattered) techniques provide a relatively high resolution, but are limited to a low imaging depth in the tissue (e.g., around 1 millimeter (mm)) that is imposed by the optical diffusion limit. When incident photons reach this limit, most of them have undergone tens of scattering events, which scramble the photon paths and inhibit effective optical focusing. In contrast, diffuse optical tomography techniques can probe greater distances (e.g., centimeters) into tissue, but with relatively low resolution (e.g., resolution equal to ⅓ of the imaging depth). One challenge of these techniques is that the randomized paths of diffuse photons render image reconstruction mathematically ill-posed. An additional limitation to each technique is that the bone analysis from optical imaging does not provide an on-site chemical composition of the bone tissue and, therefore, requires additional time to perform analysis of the sample (e.g., via a biopsy). Further, the Ballistic imaging elements and diffuse optical tomography imaging elements can be positioned at different locations and/or orientations when imaging tissue. Unfortunately, the resulting varying trajectory of the acoustic emissions, in conjunction with ill-posed positioning between the Ballistic and diffuse optical tomography imaging elements, can lead to inconsistent interpretation of the optical output. Still further, it may be difficult for a surgeon to visually identify features of the analyzed tissue during a surgical procedure. For example, a diffuse optical tomography imaging element may be used to help identify diseased bone tissue to be excised, but the surgeon (or robotic surgery apparatus) may be unable to determine, for example, margins of the diseased tissue identified by the diffuse optical tomography imaging element. This can lead to inaccurate excisions, inaccurate biopsy diagnoses resulting from analysis of incorrect bone tissue, and can complicate surgical steps.

To overcome one or more of these technical deficiencies in conventional methods, systems, and apparatuses disclosed herein include a tissue mapper device configured to address the shortcomings of the methods discussed above. For example, the tissue mapper device can include a multiplexing imaging system that can take multiple types of measurements and correlate the measurements with known cases in order to address the shortcomings of the methods discussed above. Additionally, or alternatively, the tissue mapper device can capture image data of tissue analyzed by the multiplexing imaging system to generate one or more three-dimensional ("3D") maps of, for example, anatomical element, target tissue, etc. The 3D map(s) can be generated in real-time to assist with surgical procedures and/or provide a real-time diagnosis of the target tissue.

The multiplexing imaging system can include a hybrid imaging component that is configured to perform multiple types of measurements from a single device. For example, the multiplexing imaging system can include a hybrid or multisampling MWPM component or unit (sometimes referred to herein as the "hybrid MWPM component" and/or the "hybrid MWPM unit") configured to perform multiple types of multi-wavelength measurements. For example, the hybrid MWPM component can generate a BMD value, MWPM value, $\mu_a$ value, and/or various other values of the same region. One result is that the hybrid MWPM component, and the associated systems and methods, can provide an accurate, real-time diagnosis of an individual's bone condition (e.g., bone mass, bone density, normal bone, cancerous bone, osteoporosis, clinical osteopenia, and the like). Another result is that the hybrid MWPM component, and the associated systems and methods, can generate a 3D map of the individual's bone in real-time and present the 3D map to a surgeon, doctor, or other medical professional.

In various embodiments, the multiplexing imaging system can include various other hybrid imaging components in addition to (or in alternative to) the hybrid MWPM component. By way of example, the multiplexing imaging system can include a hybrid x-ray component (e.g., configured to take multiple x-rays at varying wavelengths that are reflected differently by tissue). In various embodiments, the multiplexing imaging system can include an acoustic component (e.g., an ultrasound and/or MWPM component), an x-ray component, a CT scan component, and/or a component for any other suitable wave-based measurement. As discussed in more detail below, these components can be combined in a single device (e.g., thereby taking measurements from a single, known position) and/or from multiple devices with a well-defined position and/or orientation with respect to each other. For example, each of the imaging components can be integrated into an end-effector on a robotic surgical apparatus to take the measurements. In another example, one or more of the measurements can be taken by a device pre-operation and integrated with other measurements. In a specific, non-limiting example, imaging from an x-ray taken pre-operation can be combined with ultrasound and/or MWPM measurements taken during an operation.

Advantageously, the multiplexing imaging system can analyze the tissue from a single imaging reference position or range of known positions (e.g., multiple positions with known relative positions to create a well-posed relationship) to enable position-independent correlating of the values. In single imaging reference position embodiments, output from the multiple sensing elements can be directly combined to provide a composite analysis. For example, the system can select and process (e.g., weight, filter, etc.) output from one or more of the multiple sensing elements. The processed output can then be combined with output (e.g., image data, images, video, etc.) from any other devices (e.g., imaging devices, cameras, X-ray machines, and the like). In embodiments in which the multiple sensing elements are imaging elements, the outputted data can be quickly combined via the well-posed problem to provide a composite analysis. For example, relative positions between the sensing elements can be stored by the system. The system can then process the data (e.g., transform data, modify or scale data, etc.) to provide for enhanced interpretation by a physician. Systems can store transformation matrices that can be used to combine outputs from sensing elements located at different positions during tissue analysis. Advantageously, the transformation matrices allow for accurate analysis the same tissues, features, or the like using multiple sensing elements. Further, the resulting composite analysis can then be overlaid onto image data (e.g., 3D renderings, topological maps, pictures, video, or other image data) to produce a diagnostic image or map (sometimes referred to herein as a "composite image"). The composite image can be annotated by a user, a system programmed for annotation, etc. to facilitate user review.

The methods disclosed herein can then combine the various measurements taken by the multiplexing imaging system to take advantage of the strength of various techniques and to generate a plurality of nodes (e.g., in the case of the hybrid MWPM unit, the BMD value may accurately measure an amount of non-organic material, the MWPM value can accurately assess bone matrixes, and the absorption spectrum ($\mu_a$) value can accurately measure organic material). The resulting values can be selected and correlated to generate one or more multiplexed measurements based on, for example, patient information (e.g., age, condition, etc.), accuracy scores for the individual values, machine-learning models, and/or various combinations thereof. In some embodiments, the multiplexing imaging system includes multiple hybrid imaging components positioned and configured to direct acoustic energy at the same volume or area of tissue. The methods disclosed herein can then correlate the combined measurements to reference cases to identify similar individuals with known bone conditions, then the reference cases (and the combined measurements) to diagnose the individual's bone condition.

Accordingly, the systems and methods disclosed herein provide an accurate, real-time assessment of the individual's bone condition without requiring exposure to radiation and/or the use of expensive medical procedures.

Embodiments of the present disclosure will be described more thoroughly from now on with reference to the accompanying drawings. Like numerals represent like elements throughout the several figures, and in which example embodiments are shown. However, embodiments of the claims can be embodied in many different forms and should not be construed as limited to the embodiments set forth herein. The examples set forth herein are non-limiting examples and are merely examples, among other possible examples. Throughout this specification, plural instances (e.g., "602") can implement components, operations, or structures (e.g., "602a") described as a single instance. Further, plural instances (e.g., "602") refer collectively to a set of components, operations, or structures (e.g., "602a") described as a single instance. The description of a single component (e.g., "602a") applies equally to a like-numbered component (e.g., "602b") unless indicated otherwise. These and other aspects, features, and implementations can be expressed as methods, apparatus, systems, components, program products, means or steps for performing a function, and in other ways. These and other aspects, features, and implementations will become apparent from the following descriptions, including the claims.

DESCRIPTION OF THE FIGURES

FIG. 1 is a block diagram illustrating an example surgical system 100 ("system 100") in accordance with some embodiments of the present technology. The system 100 includes various surgical and medical equipment (e.g., a patient monitor 112) located within an operating room 102 or a doctor's office 110, a console 108 for performing surgery or other patient care, and a database 106 for storing electronic health records. The console 108 is the same as or similar to the console 420 illustrated and described in more detail with reference to FIG. 4A. The system 100 is implemented using the components of the example computer system 300 illustrated and described in more detail with reference to FIG. 3. Likewise, embodiments of the system 100 can include different and/or additional components or can be connected in different ways.

The operating room 102 is a facility, e.g., within a hospital, where surgical operations are carried out in an aseptic environment. Proper surgical procedures require a sterile field. In some embodiments, the sterile field is maintained in the operating room 102 in a medical care facility such as a hospital, the doctor's office 110, or outpatient surgery center.

In some embodiments, the system 100 includes one or more medical or surgical patient monitors 112. The monitors 112 can include a vital signs monitor (a medical diagnostic instrument), which can be a portable, battery powered, multi-parametric, vital signs monitoring device used for both ambulatory and transport applications as well as bedside monitoring. The vital signs monitor can be used with an isolated data link to an interconnected portable computer or the console 108, allowing snapshot and trended data from the vital signs monitor to be printed automatically at the console 108, and also allowing default configuration settings to be downloaded to the vital signs monitor. The vital signs monitor is capable of use as a stand-alone unit as well as part of a bi-directional wireless communications network that includes at least one remote monitoring station (e.g., the console 108). The vital signs monitor can measure multiple physiological parameters of a patient wherein various sensor output signals are transmitted either wirelessly or by means of a wired connection to at least one remote site, such as the console 108.

In some embodiments, the monitors 112 include a heart rate monitor, which is a sensor and/or a sensor system applied in the context of monitoring heart rates. The heart rate monitor measures, directly or indirectly, any physiological condition from which any relevant aspect of heart rate can be gleaned. For example, some embodiments of the heart rate monitor measure different or overlapping physiological conditions to measure the same aspect of heart rate. Alternatively, some embodiments measure the same, different, or overlapping physiological conditions to measure different aspects of heart rate, e.g., number of beats, strength of beats, regularity of beats, beat anomalies, etc.

In some embodiments, the monitors 112 include a pulse oximeter or SpO2 monitor, which is a plethysmograph or any instrument that measures variations in the size of an organ or body part of the patient on the basis of the amount of blood passing through or present in the part. The pulse oximeter is a type of plethysmograph that determines the oxygen saturation of the blood by indirectly measuring the oxygen saturation of the patient's blood (as opposed to measuring oxygen saturation directly through a blood sample) and changes in blood volume in the skin. The pulse oximeter can include a light sensor that is placed at a site on the patient, usually a fingertip, toe, forehead, or earlobe, or in the case of a neonate, across a foot. Light, which can be produced by a light source integrated into the pulse oximeter, containing both red and infrared wavelengths, is directed onto the skin of the patient, and the light that passes through the skin is detected by the pulse oximeter. The intensity of light in each wavelength is measured by the pulse oximeter over time. The graph of light intensity versus time is referred to as the photoplethysmogram (PPG) or, more commonly, simply as the "pleth." From the waveform of the PPG, it is possible to identify the pulse rate of the patient and when each individual pulse occurs. In addition, by comparing the intensities of two wavelengths when a pulse occurs, it is possible to determine blood oxygen saturation of hemoglobin in arterial blood. This relies on the observation that highly oxygenated blood will relatively absorb more red light and less infrared light than blood with a lower oxygen saturation.

In some embodiments, the monitors 112 include an end tidal CO2 monitor or capnography monitor used for measurement of the level of carbon dioxide that is released at the end of an exhaled breath (referred to as end tidal carbon dioxide, ETCO2). An end tidal CO2 monitor or capnography monitor is widely used in anesthesia and intensive care. ETCO2 can be calculated by plotting expiratory CO2 with time. Further, ETCO2 monitors are important for the measurement of applications such as cardiopulmonary resuscitation (CPR), airway assessment, procedural sedation and analgesia, pulmonary diseases such as obstructive pulmonary disease, pulmonary embolism, etc., heart failure, metabolic disorders, etc. The end tidal CO2 monitor can be configured as side stream (diverting) or mainstream (non-diverting). A diverting end tidal CO2 monitor transports a portion of a patient's respired gases from the sampling site to the end tidal CO2 monitor while a non-diverting end tidal CO2 monitor does not transport gas away. Also, measurement by the end tidal CO2 monitor is based on the absorption of infrared light by carbon dioxide where exhaled gas passes through a sampling chamber containing an infrared light source and photodetector on both sides. Based on the amount of infrared light reaching the photodetector, the amount of carbon dioxide present in the gas can be determined.

In some embodiments, the monitors 112 include a blood pressure monitor that measures blood pressure, particularly in arteries. The blood pressure monitor uses a non-invasive technique (by external cuff application) or an invasive technique (by a cannula needle inserted in artery, used in the operating room 102) for measurement. The non-invasive method (referred to as a sphygmomanometer) works by measurement of force exerted against arterial walls during (i) ventricular systole (i.e., systolic blood pressure occurs when the heart beats and pushes blood through the arteries) and (ii) ventricular diastole (i.e., diastolic blood pressure occurs when the heart rests and is filling with blood) thereby measuring systole and diastole, respectively. The blood pressure monitor can be of three types: automatic/digital, manual (aneroid-dial), and manual (mercury-column). The sphygmomanometer can include a bladder, a cuff, a pressure meter, a stethoscope, a valve, and a bulb. The cuff inflates until it fits tightly around the patient's arm, cutting off the blood flow, and then the valve opens to deflate it. The blood pressure monitor operates by inflating a cuff tightly around the arm; as the cuff reaches the systolic pressure, blood begins to flow in the artery, creating a vibration, which is detected by the blood pressure monitor, which records the systolic pressure. The techniques used for measurement can be auscultatory or oscillometric.

In some embodiments, the monitors 112 include a body temperature monitor. The body temperature monitor measures the temperature invasively or non-invasively by placement of a sensor into organs such as bladder, rectum, esophagus, tympanum, etc., and mouth, armpit, etc., respectively. The body temperature monitor is of two types: contact and non-contact. Temperature can be measured in two forms: core temperature and peripheral temperature. Temperature measurement can be done by thermocouples, resistive temperature devices (RTDs, thermistors), infrared radiators, bimetallic devices, liquid expansion devices, molecular change-of-state, and silicon diodes. A body temperature monitor commonly used for the measurement of temperature includes a temperature sensing element (e.g., temperature sensor) and a means for converting to a numerical value.

In some embodiments, the monitors 112 measure respiration rate or breathing rate—the rate at which breathing occurs—and which is measured by the number of breaths the patient takes per minute. The rate is measured when a person is at rest and simply involves counting the number of breaths for one minute by counting how many times the chest rises. Normal respiration rates for an adult patient at rest are in the range: 12 to 16 breaths per minute. A variation can be an indication of an abnormality/medical condition or the patient's demographic parameters. The monitors 112 can indicate hypoxia, a condition with low levels of oxygen in the cells, or hypercapnia, a condition in which high levels of carbon dioxide are in the bloodstream. Pulmonary disorders, asthma, anxiety, pneumonia, heart diseases, dehydration, and drug overdose are some abnormal conditions, which can cause a change to the respiration rate, thereby increasing or reducing the respiration rate from normal levels.

In some embodiments, the monitors 112 measure an electrocardiogram (EKG or ECG), a representation of the electrical activity of the heart (graphical trace of voltage versus time) by placement of electrodes on skin/body surface. The electrodes capture the electrical impulse, which travels through the heart causing systole and diastole or the pumping of the heart. This impulse provides information related to the normal functioning of the heart and the production of impulses. A change can occur due to medical conditions such as arrhythmias (tachycardia, where the heart rate becomes faster, and bradycardia, where the heart rate becomes slower), coronary heart disease, heart attacks, or cardiomyopathy. The instrument used for measurement of the electrocardiogram is called an electrocardiograph, which measures the electrical impulses by the placement of electrodes on the surface of the body and represents the ECG by a PQRST waveform. A PQRST wave is read as: P wave, which represents the depolarization of the left and right atrium and corresponds to atrial contraction; QRS complex, which indicates ventricular depolarization and represents the electrical impulse as it spreads through the ventricles; and T wave, which indicates ventricular repolarization and follows the QRS complex.

In some embodiments, the monitors 112 perform neuromonitoring, also called intraoperative neurophysiological monitoring (IONM). For example, the monitors 112 assess functions and changes in the brain, brainstem, spinal cord, cranial nerves, and peripheral nerves during a surgical procedure on these organs. Monitoring includes both continuous monitoring of neural tissue as well as the localization of vital neural structures. IONM measures changes in these organs where the changes are indicative of irreversible damage or injuries in the organs, aiming at reducing the risk of neurological deficits after operations involving the nervous system. Monitoring is effective in localization of anatomical structures, including peripheral nerves and the sensorimotor cortex, which helps in guiding the surgeon during dissection. Electrophysiological modalities employed in neuromonitoring are an extracellular single unit and local field recordings (LFP), somatosensory evoked potential (SSEP), transcranial electrical motor evoked potentials (TCeMEP), electromyography (EMG), electroencephalography (EEG), and auditory brainstem response (ABR). The use of neurophysiological monitoring during surgical procedures requires anesthesia techniques to avoid interference and signal alteration due to anesthesia.

In some embodiments, the monitors 112 measure motor evoked potential (MEP), electrical signals that are recorded from descending motor pathways or muscles following stimulation of motor pathways within the brain. MEP is determined by measurement of the action potential elicited by non-invasive stimulation of the motor cortex through the scalp. MEP is for intraoperative monitoring and neurophysiological testing of the motor pathways specifically during spinal procedures. The technique of monitoring for measurement of MEP is defined based on parameters, such as a site of stimulation (motor cortex or spinal cord), method of stimulation (electrical potential or magnetic field), and site of recording (spinal cord or peripheral mixed nerve and muscle). The target site is stimulated by the use of electrical or magnetic means.

In some embodiments, the monitors 112 measure somatosensory evoked potential (SSEP or SEP): the electrical signals generated by the brain and the spinal cord in response to sensory stimulus or touch. SSEP is used for intraoperative neurophysiological monitoring in spinal surgeries. The measurements are reliable, which allows for continuous monitoring during a surgical procedure. The sensor stimulus commonly given to the organs can be auditory, visual, or somatosensory SEPs and applied on the skin, peripheral nerves of the upper limbs, lower limbs, or scalp. The stimulation technique can be mechanical, electrical (provides larger and more robust responses), or intraoperative spinal monitoring modality.

In some embodiments, the monitors 112 provide electromyography (EMG): the evaluation and recording of electrical signals or electrical activity of the skeletal muscles. An electromyography instrument, electromyograph, or electromyogram for the measurement of the EMG activity records electrical activity produced by skeletal muscles and evaluates the functional integrity of individual nerves. The nerves monitored by an EMG instrument can be intracranial, spinal, or peripheral nerves. The electrodes used for the acquisition of signals can be invasive or non-invasive electrodes. The technique used for measurement can be spontaneous or triggered. Spontaneous EMG refers to the recording of myoelectric signals such as compression, stretching, or pulling of nerves during surgical manipulation Spontaneous EMG is recorded by the insertion of a needle electrode. Triggered EMG refers to the recording of myoelectric signals during stimulation of a target site such as a pedicle screw with incremental current intensities.

In some embodiments, the monitors 112 provide electroencephalography (EEG), measuring the electrical signals in the brain. Brain cells communicate with each other through electrical impulses. EEG can be used to help detect potential problems associated with this activity. An electroencephalograph is used for the measurement of EEG activity. Electrodes ranging from 8 to 16 pairs are attached to the scalp, where each pair of electrodes transmits a signal to one or more recording channels. EEG is a modality for intraoperative neurophysiological monitoring and assessing cortical perfusion and oxygenation during a variety of vascular, cardiac, and neurosurgical procedures. The waves produced by EEG are alpha, beta, theta, and delta.

In some embodiments, the monitors 112 include sensors, such as microphones or optical sensors, that produce images or video captured from at least one of multiple imaging devices, for example, cameras attached to manipulators or end effectors, cameras mounted to the ceiling or other surface above the surgical theater, or cameras mounted on a tripod or other independent mounting device. In some embodiments, the cameras are body worn by a surgeon or other surgical staff, cameras are incorporated into a wearable device, such as an augmented reality device like Google Glass™, or cameras are integrated into an endoscopic, microscopic, or laparoscopic device. In some embodiments, a camera or other imaging device (e.g., ultrasound) present in the operating room 102 is associated with one or more areas in the operating room 102. The sensors can be associated with measuring a specific parameter of the patient, such as respiratory rate, blood pressure, blood oxygen level, heart rate, etc.

In some embodiments, the system 100 includes a medical visualization apparatus 114 used for visualization and analysis of objects (preferably three-dimensional (3D) objects) in the operating room 102. The medical visualization apparatus 114 provides the selection of points at surfaces, selection of a region of interest, or selection of objects. The medical visualization apparatus 114 can also be used for diagnosis, treatment planning, intraoperative support, documentation, or educational purposes. The medical visualization apparatus 114 can further include microscopes, endoscopes/arthroscopes/laparoscopes, fiber optics, surgical lights, high-definition monitors, operating room cameras, etc. 3D visualization software provides visual representations of scanned body parts via virtual models, offering significant depth and nuance to static two-dimensional medical images. The software facilitates improved diagnoses, narrowed surgical operation learning curves, reduced operational costs, and shortened image acquisition times.

In some embodiments, the system 100 includes an instrument 118 such as an endoscope, arthroscope, or laparoscope for minimally invasive surgery (MIS), in which procedures are performed by cutting a minimal incision in the body. An endoscope refers to an instrument used to visualize, diagnose, and treat problems inside hollow organs where the instrument is inserted through natural body openings such as the mouth or anus. An endoscope can perform a procedure as follows: a scope with a tiny camera attached to a long, thin tube is inserted. The doctor moves it through a body passageway or opening to see inside an organ. It can be used for diagnosis and surgery (such as for removing polyps from the colon). An arthroscope refers to an instrument used to visualize, diagnose, and treat problems inside a joint by a TV camera inserted through small portals/incisions and to perform procedures on cartilage, ligaments, tendons, etc. An arthroscope can perform the procedure as follows: a surgeon makes a small incision in a patient's skin and inserts a pencil-sized instrument with a small lens and lighting system to magnify the target site (joint) and viewing of the interior of the joint by means of a miniature TV camera and then performs the procedure. A laparoscope refers to an instrument used to visualize, diagnose, and treat problems inside soft organs like the abdomen and pelvis by a TV camera inserted through small portals/incisions and to perform procedures.

In some embodiments, the system 100 includes fiber optics 120, which refer to flexible, transparent fiber made by drawing glass (silica) or plastic to a diameter slightly thicker than that of a human hair. Fiber optics 120 are arranged in bundles called optical cables and used to transmit light signals across long distances. Fiber optics 120 are used most often as a means to transmit light between the two ends of the fiber and find wide usage in the medical field. Traditional surgery requires sizable and invasive incisions to expose internal organs and operate on affected areas, but with fiber optics 120 much smaller surgical incisions can be performed. Fiber optics 120 contain components such as a core, cladding, and buffer coating. Fiber optics 120 can be inserted in hypodermic needles and catheters, endoscopes, operation theater tools, ophthalmological tools, and dentistry tools. Fiber optic sensors include a light source, optical fiber, external transducer, and photodetector. Fiber optic sensors can be intrinsic or extrinsic. Fiber optic sensors can be categorized into four types: physical, imaging, chemical, and biological.

In some embodiments, the system 100 includes surgical lights 122 (referred to as operating lights) that perform illumination of a local area or cavity of the patient. Surgical lights 122 play an important role in illumination before, during, and after a medical procedure. Surgical lights 122 can be categorized by lamp type as conventional (incandescent) and LED (light-emitting diode). Surgical lights 122 can be categorized by mounting configuration as ceiling-mounted, wall-mounted, or floor stand. Surgical lights 122 can be categorized by type as tungsten, quartz, xenon halogens, and/or LEDs. Surgical lights 122 include sterilizable handles, which allow the surgeon to adjust light positions. Some important factors affecting surgical lights 122 can be illumination, shadow management (cast shadows and contour shadows), the volume of light, heat management, or fail-safe surgical lighting.

In some embodiments, the system 100 includes a surgical tower 128, e.g., used in conjunction with the robotic surgical system 160 disclosed herein, for MIS. The surgical tower 128 includes instruments used for performing MIS or surgery, which is performed by creating small incisions in the body. The instruments are also referred to as minimally invasive devices or minimally invasive access devices. The procedure of performing MIS can also be referred to as a minimally invasive procedure. MIS is a safer, less invasive, and more precise surgical procedure. Some medical procedures where the surgical tower 128 is useful and widely used are procedures for lung, gynecological, head and neck, heart, and urological conditions. MIS can be robotic or non-robotic/endoscopic. MIS can include endoscopic, laparoscopic, arthroscopic, natural orifice intraluminal, and natural orifice transluminal procedures. A surgical tower access device can also be designed as an outer sleeve and an inner sleeve that telescopingly or slidably engage with one another. When a telescope is used to operate on the abdomen, the procedure is called laparoscopy. The surgical tower 128 typically includes access to a variety of surgical tools, such as for electrocautery, radiofrequency, lasers, sensors, etc.

In some embodiments, radiofrequency (RF) is used in association with MIS devices. The RF can be used for the treatment of skin by delivering it to the skin through a minimally invasive surgical tool (e.g., fine needles), which does not require skin excision. The RF can be used for real-time tracking of MIS devices such as laparoscopic instruments. The RF can provide radiofrequency ablation to a patient suffering from atrial fibrillation through smaller incisions made between the ribs. The RF can be used to perform an endoscopic surgery on the body such as the spine by delivery of RF energy.

In some embodiments, the system 100 includes an instrument 130 to perform electrocautery for burning a part of the body to remove or close off a part of it. Various physiological conditions or surgical procedures require the removal of body tissues and organs, a consequence of which is bleeding. In order to achieve hemostasis and for removing and sealing all blood vessels that are supplied to an organ after surgical incision, the electrocautery instrument 130 can be used. For example, after removing part of the liver for removal of a tumor, etc., blood vessels in the liver must be sealed individually. The electrocautery instrument 130 can be used for sealing living tissue such as arteries, veins, lymph nodes, nerves, fats, ligaments, and other soft tissue structures. The electrocautery instrument 130 can be used in applications such as surgery, tumor removal, nasal treatment, or wart removal. Electrocautery can operate in two modes, monopolar or bipolar. The electrocautery instrument can 130 consist of a generator, a handpiece, and one or more electrodes.

In some embodiments, the system 100 includes a laser 132 used in association with MIS devices. The laser 132 can be used in MIS with an endoscope. The laser 132 is attached to the distal end of the endoscope and steered at high speed by producing higher incision quality than with existing surgical tools thereby minimizing damage to surrounding tissue. The laser 132 can be used to perform MIS using a laparoscope in the lower and upper gastrointestinal tract, eye, nose, and throat. The laser 132 is used in MIS to ablate soft tissues, such as a herniated spinal disc bulge.

In some embodiments, sensors 134 are used in association with MIS devices and the robotic surgical system 160 described herein. The sensors 134 can be used in MIS for tactile sensing of surgical tool-tissue interaction forces. During MIS, the field of view and workspace of surgical tools are compromised due to the indirect access to the anatomy and lack of surgeon's hand-eye coordination. The sensors 134 provide a tactile sensation to the surgeon by providing information regarding shape, stiffness, and texture of organ or tissue (different characteristics) to the surgeon's hands through a sense of touch. This detects a tumor through palpation, which exhibits a "tougher" feel than that of healthy soft tissue, pulse felt from blood vessels, and abnormal lesions. The sensors 134 can output shape, size, pressure, softness, composition, temperature, vibration, shear, and normal forces. The sensors 134 can be electrical or optical, consisting of capacitive, inductive, piezoelectric, piezoresistive, magnetic, and auditory. The sensors 134 can be used in robotic or laparoscopic surgery, palpation, biopsy, heart ablation, and valvuloplasty.

In some embodiments, the system 100 includes an imaging system 136 (instruments are used for the creation of images and visualization of the interior of a human body for diagnostic and treatment purposes). The imaging system 136 is used in different medical settings and can help in the screening of health conditions, diagnosing causes of symptoms, or monitoring of health conditions. The imaging system 136 can include various imaging techniques such as X-ray, fluoroscopy, magnetic resonance imaging (MRI), ultrasound, endoscopy, elastography, tactile imaging, thermography, medical photography, and nuclear medicine, e.g., positron emission tomography (PET). Some factors which can drive the market are cost and clinical advantages of medical imaging modalities, a rising share of ageing populations, increasing prevalence of cardiovascular or lifestyle diseases, and increasing demand from emerging economies.

In some embodiments, the imaging system 136 includes X-ray medical imaging instruments that use X-ray radiation (i.e., X-ray range in the electromagnetic radiation spectrum) for the creation of images of the interior of the human body for diagnostic and treatment purposes. An X-ray instrument is also referred to as an X-ray generator. It is a non-invasive instrument based on different absorption of X-rays by tissues based on their radiological density (radiological density is different for bones and soft tissues). For the creation of an image by the X-ray instrument, X-rays produced by an X-ray tube are passed through a patient positioned to the detector. As the X-rays pass through the body, images appear in shades of black and white, depending on the type and densities of tissue the X-rays pass through. Some of the applications where X-rays are used can be bone fractures, infections, calcification, tumors, arthritis, blood vessel blockages, digestive problems, or heart problems. The X-ray instrument can consist of components such as an X-ray tube, operating console, collimator, grid, detector, radiographic film, etc.

In some embodiments, the imaging system 136 includes Mill medical imaging instruments that use powerful magnets for the creation of images of the interior of the human body for diagnostic and treatment purposes. Some of the applications where MM can be used can be brain/spinal cord anomalies, tumors in the body, breast cancer screening, joint injuries, uterine/pelvic pain detection, or heart problems. For the creation of the image by an Mill instrument, magnetic resonance is produced by powerful magnets, which produce a strong magnetic field that forces protons in the body to align with that field. When a radiofrequency current is then pulsed through the patient, the protons are stimulated, and spin out of equilibrium, straining against the pull of the magnetic field. Turning off the radiofrequency field allows detection of energy released by realignment of protons with the magnetic field by MRI sensors. The time taken by the protons for realignment with the magnetic field and energy release is dependent on environmental factors and the chemical nature of the molecules. MM is more widely suitable for imaging of non-bony parts or soft tissues of the body. MM can be less harmful as it does not use damaging ionizing radiation as in the X-ray instrument. MM instruments can consist of magnets, gradients, radiofrequency systems, or computer control systems. Some areas where imaging by MM should be prohibited can be people with implants.

In some embodiments, the imaging system 136 uses computed tomography imaging (CT) that uses an X-ray radiation (i.e., X-ray range in the electromagnetic radiation spectrum) for the creation of cross-sectional images of the interior of the human body. CT refers to a computerized X-ray imaging procedure in which a narrow beam of X-rays is aimed at a patient and quickly rotated around the body, producing signals that are processed by the machine's computer to generate cross-sectional images—or "slices"— of the body. A CT instrument is different from an X-ray instrument as it creates 3-dimensional (3D) cross-sectional images of the body while the X-ray instrument creates 2-dimensional (2D) images of the body; the 3D cross-sectional images are created by taking images from different angles, which is done by taking a series of tomographic images from different angles. The diverse images are collected by a computer and digitally stacked to form a 3D image of the patient. For creation of images by the CT instrument, a CT scanner uses a motorized X-ray source that rotates around the circular opening of a donut-shaped structure called a gantry while the X-ray tube rotates around the patient shooting narrow beams of X-rays through the body. Some of the applications where CT can be used can be blood clots; bone fractures, including subtle fractures not visible on X-ray; or organ injuries.

In some embodiments, the imaging system 136 includes ultrasound imaging, also referred to as sonography or ultrasonography, that uses ultrasound or sound waves (also referred to as acoustic waves) for the creation of cross-sectional images of the interior of the human body. Ultrasound waves in the imaging system 136 can be produced by a piezoelectric transducer, which produces sound waves and sends them into the body. The sound waves that are reflected are converted into electrical signals, which are sent to an ultrasound scanner. Ultrasound instruments can be used for diagnostic and functional imaging or for therapeutic or interventional procedures. Some of the applications where ultrasound can be used are diagnosis/treatment/guidance during medical procedures (e.g., biopsies, internal organs such as liver/kidneys/pancreas, fetal monitoring, etc.), in soft tissues, muscles, blood vessels, tendons, or joints. Ultrasound can be used for internal imaging (where the transducer is placed in organs, e.g., vagina) and external imaging (where the transducer is placed on the chest for heart monitoring or the abdomen for fetal monitoring). An ultrasound machine can consist of a monitor, keyboard, processor, data storage, probe, and transducer.

In some embodiments, the system 100 includes a stereotactic navigation system 138 that uses patient imaging (e.g., CT, MRI) to guide surgeons in the placement of specialized surgical instruments and implants. The patient images are taken to guide the physician before or during the medical procedure. The stereotactic navigation system 138 includes a camera having infrared sensors to determine the location of the tip of the probe being used in the surgical procedure. This information is sent in real-time so that the surgeons have a clear image of the precise location where they are working in the body. The stereotactic navigation system 138 can be framed (requires attachment of a frame to the patient's head using screws or pins) or frameless (does not require the placement of a frame on the patient's anatomy). The stereotactic navigation system 138 can be used for diagnostic biopsies, tumor resection, bone preparation/implant placement, placement of electrodes, otolaryngologic procedures, or neurosurgical procedures.

In some embodiments, the system 100 includes an anesthesiology machine 140 that is used to generate and mix medical gases, such as oxygen or air, and anesthetic agents to induce and maintain anesthesia in patients. The anesthesiology machine 140 delivers oxygen and anesthetic gas to the patient and filters out expiratory carbon dioxide. The anesthesiology machine 140 can perform functions such as providing oxygen (O2), accurately mixing anesthetic gases and vapors, enabling patient ventilation, and minimizing anesthesia-related risks to patients and staff. The anesthesiology machine 140 can include the following essential components: a source of O2, O2 flowmeter, vaporizer (anesthetics include isoflurane, halothane, enflurane, desflurane, sevoflurane, and methoxyflurane), patient breathing circuit (tubing, connectors, and valves), and scavenging system (removes any excess anesthetics gases). The anesthesiology machine 140 can be divided into three parts: the high pressure system, the intermediate pressure system, and the low pressure system. The process of anesthesia starts with oxygen flow from a pipeline or cylinder through the flowmeter; the O2 flows through the vaporizer and picks up the anesthetic vapors; the O2-anesthetic mix then flows through the breathing circuit and into the patient's lungs, usually by spontaneous ventilation or normal respiration.

In some embodiments, the system 100 includes a surgical bed 142 equipped with mechanisms that can elevate or lower the entire bed platform; flex, or extend individual components of the platform; or raise or lower the head or the feet of the patient independently. The surgical bed 142 can be an operation bed, cardiac bed, amputation bed, or fracture bed. Some essential components of the surgical bed 142 can be a bed sheet, woolen blanket, bath towel, and bed block. The surgical bed 142 can also be referred to as a post-operative bed, which refers to a special type of bed made for the patient who is coming from the operation theater or from another procedure that requires anesthesia. The surgical bed 142 is designed in a manner that makes it easier to transfer an unconscious or weak patient from a stretcher/wheelchair to the bed. The surgical bed 142 should protect bed linen from vomiting, bleeding, drainage, and discharge; provide warmth and comfort to the patient to prevent shock; provide necessary positions, which are suitable for operation; protect patient from being chilled; and be prepared to meet any emergency.

In some embodiments, the system 100 includes a Jackson frame 144 (or Jackson table), which refers to a frame or table that is designed for use in spinal surgeries and can be used in a variety of spinal procedures in supine, prone, or lateral positions in a safe manner. Two peculiar features of the Jackson table 144 are the absence of central table support and an ability to rotate the table through 180 degrees. The Jackson table 144 is supported at both ends, which keeps the whole of the table free. This allows the visualization of a patient's trunk and major parts of extremities as well. The Jackson frame 144 allows the patient to be slid from the cart onto the table in the supine position with appropriate padding placed. The patient is then strapped securely on the Jackson table 144.

In some embodiments, the system 100 includes a disposable air warmer 146 (sometimes referred to as a Bair™ or Bair Hugger™). The disposable air warmer 146 is a convective temperature management system used in a hospital or surgery center to maintain a patient's core body temperature. The disposable air warmer 146 includes a reusable warming unit and a single-use disposable warming blanket for use during surgery. It can also be used before and after surgery. The disposable air warmer 146 uses convective warming consisting of two components: a warming unit and a disposable blanket. The disposable air warmer 146 filters air and then forces warm air through disposable blankets, which cover the patient. The blanket can be designed to use pressure points on the patient's body to prevent heat from reaching areas at risk for pressure sores or burns. The blanket can also include drainage holes where fluid passes through the surface of the blanket to linen underneath, which will reduce the risk of skin softening and reduce the risk of unintended cooling because of heat loss from evaporation.

In some embodiments, the system 100 includes a sequential compression device (SCD) 148 used to help prevent blood clots in the deep veins of legs. The sequential compression device 148 uses cuffs around the legs that fill with air and squeeze the legs. This increases blood flow through the veins of the legs and helps prevent blood clots. A deep vein thrombosis (DVT) is a blood clot that forms in a vein deep inside the body. Some of the risks of using the SCD 148 can be discomfort, warmth, sweating beneath the cuff, skin breakdown, nerve damage, or pressure injury.

In some embodiments, the system 100 includes a bed position controller 150, which refers to an instrument for controlling the position of the patient bed. Positioning a patient in bed is important for maintaining alignment and for preventing bedsores (pressure ulcers), foot drop, and contractures. Proper positioning is also vital for providing comfort for patients who are bedridden or have decreased mobility related to a medical condition or treatment. When positioning a patient in bed, supportive devices such as pillows, rolls, and blankets, along with repositioning, can aid in providing comfort and safety. The patient can be in the following positions in a bed: supine position, prone position, lateral position, Sims' position, Fowler's position, semi-Fowler's position, orthopedic or tripod position, or Trendelenburg position.

In some embodiments, the system 100 includes environmental controls 152. The environmental controls 152 can be operating room environmental controls for control or maintenance of the environment in the operating room 102 where procedures are performed to minimize the risk of airborne infection and to provide a conducive environment for everyone in the operating room 102 (e.g., surgeon, anesthesiologist, nurses, and patient). Some factors that can contribute to poor quality in the environment of the operating room 102 are temperature, ventilation, and humidity, and those conditions can lead to profound effects on the health and work productivity of people in the operating room 102. As an example: surgeons prefer a cool, dry climate since they work under bright, hot lights; anesthesia personnel prefer a warmer, less breezy climate; patient condition demands a relatively warm, humid, and quiet environment. The operating room environmental controls can control the environment by taking care of the following factors: environmental humidity, infection control, or odor control. Humidity control can be performed by controlling the temperature of anesthesia gases; infection can be controlled by the use of filters to purify the air.

In some embodiments, the environmental controls 152 include a heating, ventilation, and air conditioning (HVAC) system for regulating the environment of indoor settings by moving air between indoor and outdoor areas, along with heating and cooling. HVAC can use a different combination of systems, machines, and technologies to improve comfort. HVAC can be necessary to maintain the environment of the operating room 102. The operating room 102 can be a traditional operating room (which can have a large diffuser array directly above the operating table) or a hybrid operating room (which can have monitors and imaging equipment 136 that consume valuable ceiling space and complicate the design process). HVAC can include three main units, for example, a heating unit (e.g., furnace or boiler), a ventilation unit (natural or forced), and an air conditioning unit (which can remove existing heat). HVAC can be made of components such as air returns, filters, exhaust outlets, ducts, electrical elements, outdoor units, compressors, coils, and blowers. The HVAC system can use central heating and AC systems that use a single blower to circulate air via internal ducts.

In some embodiments, the environmental controls 152 include an air purification system for removing contaminants from the air in the operating room 102 to improve indoor air quality. Air purification can be important in the operating room 102 as surgical site infection can be a reason for high mortality and morbidity. The air purification system can deliver clean, filtered, contaminant-free air over the surgical bed 142 using a diffuser, airflow, etc., to remove all infectious particles down and away from the patient. The air purification system can be an air curtain, multi-diffuser array, or single large diffuser (based on laminar diffuser flow) or High-Efficiency Particulate Air filter (HEPA filter). A HEPA filter protects a patient from infection and contamination using a filter, which is mounted at the terminal of the duct. A HEPA filter can be mounted on the ceiling and deliver clean, filtered air in a flow to the operating room 102 that provides a sweeping effect that pushes contaminants out via the return grilles that are usually mounted on the lower wall.

In some embodiments, the system 100 includes one or more medical or surgical tools 154. The surgical tools 154 can include orthopedic tools (also referred to as orthopedic instruments) used for treatment and prevention of deformities and injuries of the musculoskeletal system or skeleton, articulations, and locomotive system (i.e., set formed by skeleton, muscles attached to it, and the part of the nervous system that controls the muscles). A major percentage of orthopedic tools are made of plastic. The orthopedic tools can be divided into the following specialties: hand and wrist, foot and ankle, shoulder, and elbow, arthroscopic, hip, and knee. The orthopedic tools can be fixation tools, relieving tools, corrective tools, or compression-distraction tools. A fixation tool refers to a tool designed to restrict movements partially or completely in a joint, e.g., hinged splints (for preserving a certain range of movement in a joint) or rigid splints. A relieving tool refers to a tool designed to relieve pressure on an ailing part by transferring support to healthy parts of an extremity, e.g., Thomas splint and the Voskoboinikova apparatus. A corrective tool refers to a surgical tool designed to gradually correct a deformity, e.g., corsets, splints, orthopedic footwear, insoles, and other devices to correct abnormal positions of the foot. A compression-distraction tool refers to a surgical tool designed to correct acquired or congenital deformities of the extremities, e.g., curvature, shortening, and pseudarthrosis such as Gudushauri. A fixation tool can be an internal fixation tool (e.g., screws, plates) or external fixation tools used to correct a radius or tibia fracture. The orthopedic tools can be bone-holding forceps, drill bits, nail pins, hammers, staples, etc.

In some embodiments, the surgical tools 154 include a drill for making holes in bones for insertion of implants like nails, plates, screws, and wires. The drill tool functions by drilling cylindrical tunnels into bone. Drills can be used in orthopedics for performing medical procedures. If the drill does not stop immediately when used, the use of the drill on bones can have some risks, such as harm caused to bone, muscle, nerves, and venous tissues, which are wrapped by surrounding tissue. Drills vary widely in speed, power, and size. Drills can be powered as electrical, pneumatic, or battery. Drills generally can work on speeds below 1000 rpm in orthopedic settings. Temperature control of drills is an important aspect in the functioning of the drill and is dependent on parameters such as rotation speed, torque, orthotropic site, sharpness of the cutting edges, irrigation, and cooling systems. The drill can include a physical drill, power cord, electronically motorized bone drill, or rotating bone shearing incision work unit.

In some embodiments, the surgical tools 154 include a scalpel for slicing, cutting, or osteotomy of bone during orthopedic procedure. The scalpel can be designed to provide clean cuts through osseous structures with minimal loss of viable bone while sparing adjacent elastic soft tissues largely unaffected while performing a slicing procedure. This is suited for spine applications where bone must be cut adjacent to the dura and neural structures. The scalpel does not rotate but performs cutting by an ultrasonically oscillating or forward/backward moving metal tip. Scalpels can prevent injuries caused by a drill in a spinal surgery such as complications such as nerve thermal injury, grasping soft tissue, tearing dura mater, and mechanical injury.

In some embodiments, stitches (also referred to as sutures) or a sterile, surgical thread is used to repair cuts or lacerations and is used to close incisions or hold body tissues together after a surgery or an injury. Stitches can involve the use of a needle along with an attached thread. Stitches can be either absorbable (the stitches automatically break down harmlessly in the body over time without intervention) or non-absorbable (the stitches do not automatically break down over time and must be manually removed if not left indefinitely). Stitches can be based on material monofilament, multifilament, and barb. Stitches can be classified based on size. Stitches can be based on synthetic or natural material. Stitches can be coated or un-coated.

In some embodiments, the surgical tools 154 include a stapler used for fragment fixation when inter-fragmental screw fixation is not easy. When there is vast damage and a bone is broken into fragments, staples can be used between these fragments for internal fixation and bone reconstruction. For example, they can be used around joints in ankle and foot surgeries, in cases of soft tissue damage, or to attach tendons or ligaments to the bone for reconstruction surgery. Staplers can be made of surgical grade stainless steel or titanium, and they are thicker, stronger, and larger.

In some embodiments, other medical or surgical equipment, such as a set of articles, surgical tools, or objects, is used to implement or achieve an operation or activity. A medical equipment refers to an article, instrument, apparatus, or machine used for diagnosis, prevention, or treatment of a medical condition or disease, or to the detection, measurement, restoration, correction, or modification of structure/function of the body for some health purpose. The medical equipment can perform functions invasively or non-invasively. In some embodiments, the medical equipment includes components such as a sensor/transducer, a signal conditioner, a display, or a data storage unit, etc. In some embodiments, the medical equipment includes a sensor to receive a signal from instruments measuring a patient's body, a transducer for converting one form of energy to electrical energy, a signal conditioner such as an amplifier, filter, etc., to convert the output from the transducer into an electrical value, a display to provide a visual representation of the measured parameter or quantity, or a storage system to store data, which can be used for future reference. A medical equipment can perform diagnosis or provide therapy; for example, the equipment delivers air into the lungs of a patient who is physically unable to breathe, or breathes insufficiently, and moves it out of the lungs.

In some embodiments, the system includes a machine 156 to aid in breathing. The machine 156 can be a ventilator (also referred to as a respirator) that provides a patient with oxygen when they are unable to breathe on their own. A ventilator is required when a person is not able to breathe on their own. A ventilator can perform a function of gently pushing air into the lungs and allow it to come back out. The ventilator functions by delivery of positive pressure to force air into the lungs, while usual breathing uses negative pressure by the opening of the mouth, and air flows in. The ventilator can be required during surgery or after surgery. The ventilator can be required in case of respiratory failure due to acute respiratory distress syndrome, head injury, asthma, lung diseases, drug overdose, neonatal respiratory distress syndrome, pneumonia, sepsis, spinal cord injury, cardiac arrest, etc., or during surgery. The ventilator can be used with a face mask (non-invasive ventilation, where the ventilation is required for a shorter duration of time) or with a breathing tube also referred to as an endotracheal tube (invasive ventilation, where the ventilation is required for a longer duration of time). Ventilator use can have some risks such as infections, fluid build-up, muscle weakness, lung damage, etc. The ventilator can be operated in various modes, such as assist-control ventilation (ACV), synchronized intermittent-mandatory ventilation (SIMV), pressure-controlled ventilation (PCV), pressure support ventilation (PSV), pressure-controlled inverse ratio ventilation (PCIRV), airway pressure release ventilation (APRV), etc. The ventilator can include a gas delivery system, power source, control system, safety feature, gas filter, and monitor.

In some embodiments, the machine 156 is a continuous positive airway pressure (CPAP) used for the treatment of sleep apnea disorder in a patient. Sleep apnea refers to a disorder in which breathing repeatedly stops and starts while a patient is sleeping, often because throat/airways briefly collapse or something temporarily blocks them. Sleep apnea can lead to serious health problems, such as high blood pressure and heart trouble. A CPAP instrument helps the patient with sleep apnea to breathe more easily during sleep by sending a steady flow of oxygen into the nose and mouth during sleep, which keeps the airways open and helps the patient to breathe normally. The CPAP machine can work by a compressor/motor, which generates a continuous stream of pressurized air that travels through an air filter into a flexible tube. The tube delivers purified air into a mask sealed around the nose/mouth of the patient. The airstream from the instrument pushes against any blockages, opening the airways so lungs receive plenty of oxygen, and breathing does not stop as nothing obstructs oxygen. This helps the patient to not wake up to resume breathing. CPAP can have a nasal pillow mask, nasal mask, or full mask. CPAP instrument can include a motor, a cushioned mask, a tube that connects the motor to the mask, a headgear frame, and adjustable straps. The essential components can be a motor, a cushioned mask, and a tube that connects the motor to the mask.

In some embodiments, the system 100 includes surgical supplies, consumables 158, or necessary supplies for the system 100 to provide care within the hospital or surgical environment. The consumables 158 can include gloves, gowns, masks, syringes, needles, sutures, staples, tubing, catheters, or adhesives for wound dressing, in addition to other surgical tools needed by doctors and nurses to provide care. Depending on the device, mechanical testing can be carried out in tensile, compression, or flexure; in dynamic or fatigue; via impact; or with the application of torsion. The consumables 158 can be disposable (e.g., time-saving, have no risk of healthcare-associated infections, and cost-efficient) or sterilizable (to avoid cross-contamination or risk of surgical site infections).

In some embodiments, the system 100 includes a robotic surgical system 160 (sometimes referred to as a medical robotic system or a robotic system) that provides intelligent services and information to the operating room 102 and the console 108 by interacting with the environment, including human beings, via the use of various sensors, actuators, and human interfaces. The robotic surgical system 160 can be employed for automating processes in a wide range of applications, ranging from industrial (manufacturing), domestic, medical, service, military, entertainment, space, etc. The medical robotic system market is segmented by product type into surgical robotic systems, rehabilitative robotic systems, non-invasive radiosurgery robots, and hospital and pharmacy robotic systems. Robotic surgeries are performed using tele-manipulators (e.g., input devices 166 at the console 108), which use the surgeon's actions on one side to control one or more "effectors" on the other side. The medical robotic system 160 provides precision and can be used for remotely controlled, minimally invasive procedures. The robotic surgical system 160 includes computer-controlled electromechanical devices that work in response to controls (e.g., input devices 166 at the console 108) manipulated by the surgeons.

In some embodiments, the system 100 includes equipment tracking systems 162, such as RFID, which is used to tag an instrument with an electronic tag and tracks it using the tag. Typically, this could involve a centralized platform that provides details such as location, owner, contract, and maintenance history for all equipment in real-time. A variety of techniques can be used to track physical assets, including RFID, global positioning system (GPS), Bluetooth low energy (BLE), barcodes, near-field communication (NFC), Wi-Fi, etc. The equipment tracking system 162 includes hardware components, such as RFID tags, GPS trackers, barcodes, and QR codes. The hardware component is placed on the asset, and it communicates with the software (directly or via a scanner), providing the software with data about the asset's location and properties. In some embodiments, the equipment tracking system 162 uses electromagnetic fields to transmit data from an RFID tag to a reader. Reading of RFID tags can be done by portable or mounted RFID readers. The read range for RFID varies with the frequency used. Managing and locating important assets is a key challenge for tracking medical equipment. Time spent searching for critical equipment can lead to expensive delays or downtime, missed deadlines and customer commitments, and wasted labor. The problem has previously been solved by using barcode labels or manual serial numbers and spreadsheets; however, these require manual labor. The RFID tag can be passive (smaller and less expensive, read ranges are shorter, have no power of their own, and are powered by the radio frequency energy transmitted from RFID readers/antennas) or active (larger and more expensive, read ranges are longer, have a built-in power source and transmitter of their own).

In some embodiments, the system 100 includes medical equipment, computers, software, etc., located in the doctor's office 110 that is communicably coupled to the operating room 102 over the network 104. For example, the medical equipment in the doctor's office 110 can include a microscope 116 used for viewing samples and objects that cannot be seen with an unaided eye. The microscope 116 can have components such as eyepieces, objective lenses, adjustment knobs, a stage, an illuminator, a condenser, or a diaphragm. The microscope 116 works by manipulating how light enters the eye using a convex lens, where both sides of the lens are curved outwards. When light reflects off of an object being viewed under the microscope 116 and passes through the lens, it bends toward the eye. This makes the object look bigger than it is. The microscope 116 can be compound (light-illuminated and the image seen with the microscope 116 is two-dimensional), dissection or stereoscope (light-illuminated and the image seen with the microscope 116 is three-dimensional), confocal (laser-illuminated and the image seen with the microscope 116 is on a digital computer screen), scanning electron (SEM) (electron-illuminated and the image seen with the microscope 116 is in black and white), or transmission electron microscope (TEM) (electron-illuminated and the image seen with the microscope 116 is the high magnification and high resolution).

The system 100 includes an electronic health records (EHR) database 106 that contains patient records. The EHR are a digital version of patients' paper charts. The EHR database 106 can contain more information than a traditional patient chart, including, but not limited to, a patients' medical history, diagnoses, medications, treatment plans, allergies, diagnostic imaging, lab results, etc. In some embodiments, the steps for each procedure disclosed herein are stored in the EHR database 106. Electronic health records can also include data collected from the monitors 112 from historical procedures. The EHR database 106 is implemented using components of the example computer system 300 illustrated and described in more detail with reference to FIG. 3.

In some embodiments, the EHR database 106 includes a digital record of patients' health information, collected, and stored systematically over time. The EHR database 106 can include demographics, medical history, history of present illness (HPI), progress notes, problems, medications, vital signs, immunizations, laboratory data, or radiology reports. Software (in memory 164) operating on the console 108 or implemented on the example computer system 300 (e.g., the instructions 304, 308 illustrated and described in more detail with reference to FIG. 3) are used to capture, store, and share patient data in a structured way. The EHR database 106 can be created and managed by authorized providers and can make health information accessible to authorized providers across practices and health organizations, such as laboratories, specialists, medical imaging facilities, pharmacies, emergency facilities, etc. The timely availability of EHR data enables healthcare providers to make more accurate decisions and provide better care to the patients by effective diagnosis and reduced medical errors. Besides providing opportunities to enhance patient care, the EHR database 106 can also be used to facilitate clinical research by combining patients' demographics into a large pool. For example, the EHR database 106 can support a wide range of epidemiological research on the natural history of disease, drug utilization, and safety, as well as health services research.

The console 108 is a computer device, such as a server, computer, tablet, smartphone, smart speaker, etc., implemented using components of the example computer system 300 illustrated and described in more detail with reference to FIG. 3. In some embodiments, the steps for each procedure disclosed herein are stored in memory 164 on the console 108 for execution.

In some embodiments, the operating room 102 or the console 108 includes high-definition monitors 124, which refer to displays in which a clearer picture is possible than with low-definition, low-resolution screens. The high-definition monitors 124 have a higher density of pixels per inch than past standard TV screens. Resolution for the high-definition monitors 124 can be 1280×720 pixels or more (e.g., Full HD, 1920×1080; Quad HD, 2560×1440; 4K, 3840×2160; 8K, 7680×4320 pixels). The high-definition monitor 124 can operate in progressive or interlaced scanning mode. High-definition monitors used in medical applications can offer improved visibility; allow for precise and safe surgery with rich color reproduction; provide suitable colors for each clinical discipline; provide better visibility, operability with a large screen and electronic zoom, higher image quality in low light conditions, better visualization of blood vessels and lesions, and high contrast at high spatial frequencies; be twice as sensitive as conventional sensors; and make it easier to determine tissue boundaries (fat, nerves, vessels, etc.).

In some embodiments, the console 108 includes an input interface or one or more input devices 166. The input devices 166 can include a keyboard, a mouse, a joystick, any hand-held controller, or a hand-controlled manipulator, e.g., a tele-manipulator used to perform robotic surgery.

In some embodiments, the console 108, the equipment in the doctor's office 110, and the EHR database 106 are communicatively coupled to the equipment in the operating room 102 by a direct connection, such as ethernet, or wirelessly by the cloud over the network 104. The network 104 is the same as or similar to the network 314 illustrated and described in more detail with reference to FIG. 3. For example, the console 108 can communicate with the robotic surgical system 160 using the network adapter 312 illustrated and described in more detail with reference to FIG. 3.

Figure 2:
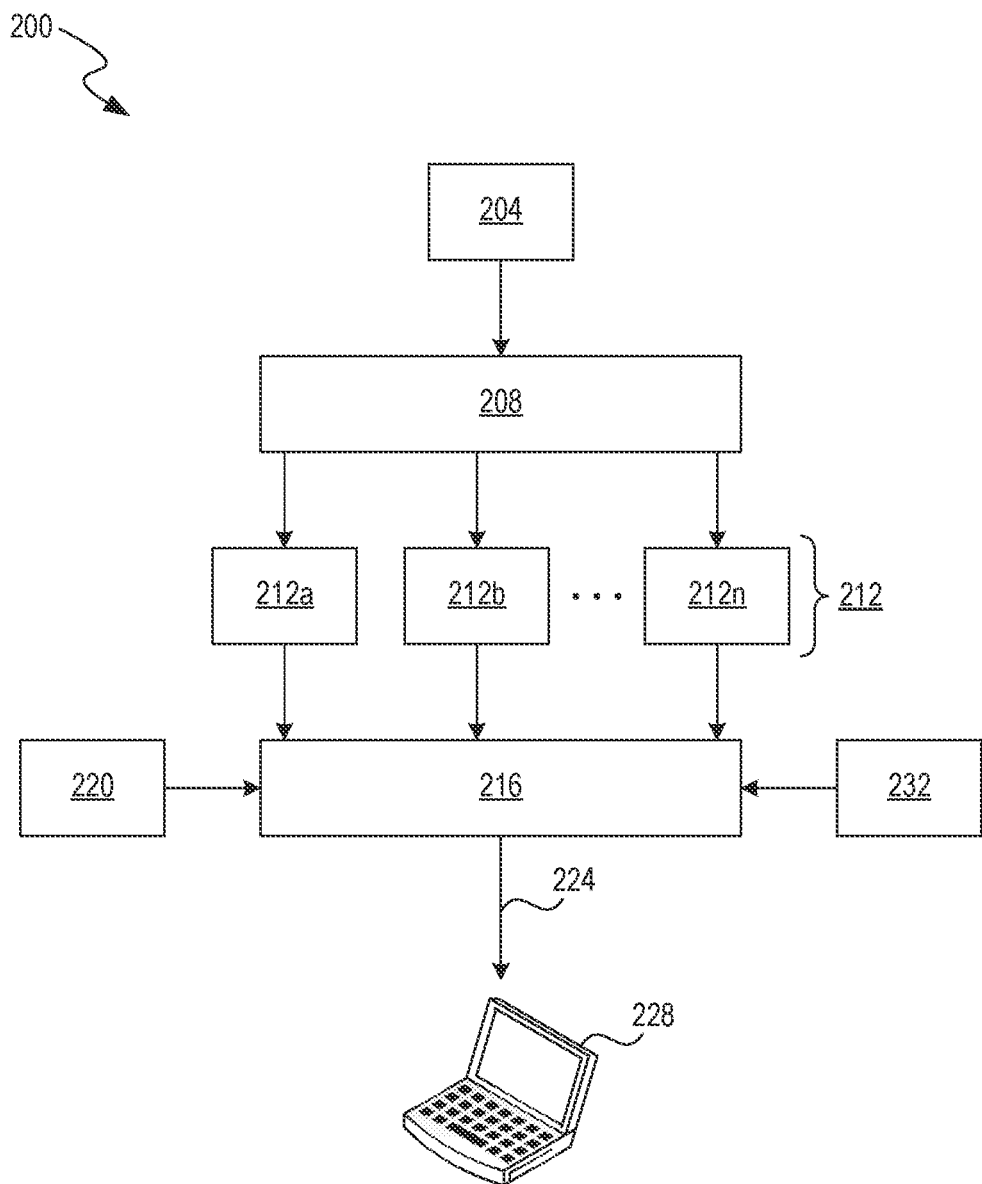
FIG. 2 is a block diagram illustrating an example machine learning (ML) system, in accordance with one or more embodiments.

FIG. 2 is a block diagram illustrating an example machine learning (ML) system 200, in accordance with one or more embodiments. The ML system 200 is implemented using components of the example computer system 300 illustrated and described in more detail with reference to FIG. 3. For example, the ML system 200 can be implemented on the console 108 using instructions programmed in the memory 164 illustrated and described in more detail with reference to FIG. 1. Likewise, embodiments of the ML system 200 can include different and/or additional components or be connected in different ways. The ML system 200 is sometimes referred to as a ML module.

The ML system 200 includes a feature extraction module 208 implemented using components of the example computer system 300 illustrated and described in more detail with reference to FIG. 3. In some embodiments, the feature extraction module 208 extracts a feature vector 212 from input data 204. For example, the input data 204 can include one or more physiological parameters measured by the monitors 112 illustrated and described in more detail with reference to FIG. 1. The feature vector 212 includes features 212a, 212b, . . . 212n. The feature extraction module 208 reduces the redundancy in the input data 204, e.g., repetitive data values, to transform the input data 204 into the reduced set of features 212, e.g., features 212a, 212b, . . . 212n. The feature vector 212 contains the relevant information from the input data 204, such that events or data value thresholds of interest can be identified by the ML model 216 by using this reduced representation. In some example embodiments, the following dimensionality reduction techniques are used by the feature extraction module 208: independent component analysis, Isomap, kernel principal component analysis (PCA), latent semantic analysis, partial least squares, PCA, multifactor dimensionality reduction, nonlinear dimensionality reduction, multilinear PCA, multilinear subspace learning, semidefinite embedding, autoencoder, and deep feature synthesis.

In alternate embodiments, the ML model 216 performs deep learning (also known as deep structured learning or hierarchical learning) directly on the input data 204 to learn data representations, as opposed to using task-specific algorithms. In deep learning, no explicit feature extraction is performed; the features 212 are implicitly extracted by the ML system 200. For example, the ML model 216 can use a cascade of multiple layers of nonlinear processing units for implicit feature extraction and transformation. Each successive layer uses the output from the previous layer as input. The ML model 216 can thus learn in supervised (e.g., classification) and/or unsupervised (e.g., pattern analysis) modes. The ML model 216 can learn multiple levels of representations that correspond to different levels of abstraction, wherein the different levels form a hierarchy of concepts. In this manner, the ML model 216 can be configured to differentiate features of interest from background features.

In alternative example embodiments, the ML model 216, e.g., in the form of a CNN generates the output 224, without the need for feature extraction, directly from the input data 204. The output 224 is provided to the computer device 228 or the console 108 illustrated and described in more detail with reference to FIG. 1. The computer device 228 is a server, computer, tablet, smartphone, smart speaker, etc., implemented using components of the example computer system 300 illustrated and described in more detail with reference to FIG. 3. In some embodiments, the steps performed by the ML system 200 are stored in memory on the computer device 228 for execution. In other embodiments, the output 224 is displayed on the high-definition monitors 124 illustrated and described in more detail with reference to FIG. 1.

A CNN is a type of feed-forward artificial neural network in which the connectivity pattern between its neurons is inspired by the organization of a visual cortex. Individual cortical neurons respond to stimuli in a restricted region of space known as the receptive field. The receptive fields of different neurons partially overlap such that they tile the visual field. The response of an individual neuron to stimuli within its receptive field can be approximated mathematically by a convolution operation. CNNs are based on biological processes and are variations of multilayer perceptrons designed to use minimal amounts of preprocessing.

The ML model 216 can be a CNN that includes both convolutional layers and max pooling layers. The architecture of the ML model 216 can be "fully convolutional," which means that variable sized sensor data vectors can be fed into it. For all convolutional layers, the ML model 216 can specify a kernel size, a stride of the convolution, and an amount of zero padding applied to the input of that layer. For the pooling layers, the model 216 can specify the kernel size and stride of the pooling.

In some embodiments, the ML system 200 trains the ML model 216, based on the training data 220, to correlate the feature vector 212 to expected outputs in the training data 220. As part of the training of the ML model 216, the ML system 200 forms a training set of features and training labels by identifying a positive training set of features that have been determined to have a desired property in question, and, in some embodiments, forms a negative training set of features that lack the property in question.

The ML system 200 applies ML techniques to train the ML model 216, that when applied to the feature vector 212, outputs indications of whether the feature vector 212 has an associated desired property or properties, such as a probability that the feature vector 212 has a particular Boolean property, or an estimated value of a scalar property. The ML system 200 can further apply dimensionality reduction (e.g., via linear discriminant analysis (LDA), PCA, or the like) to reduce the amount of data in the feature vector 212 to a smaller, more representative set of data.

The ML system 200 can use supervised ML to train the ML model 216, with feature vectors of the positive training set and the negative training set serving as the inputs. In some embodiments, different ML techniques, such as linear support vector machine (linear SVM), boosting for other algorithms (e.g., AdaBoost), logistic regression, naïve Bayes, memory-based learning, random forests, bagged trees, decision trees, boosted trees, boosted stumps, neural networks, CNNs, etc., are used. In some example embodiments, a validation set 232 is formed of additional features, other than those in the training data 220, which have already been determined to have or to lack the property in question. The ML system 200 applies the trained ML model 216 to the features of the validation set 232 to quantify the accuracy of the ML model 216. Common metrics applied in accuracy measurement include: Precision and Recall, where Precision refers to a number of results the ML model 216 correctly predicted out of the total it predicted, and Recall is a number of results the ML model 216 correctly predicted out of the total number of features that had the desired property in question. In some embodiments, the ML system 200 iteratively re-trains the ML model 216 until the occurrence of a stopping condition, such as the accuracy measurement indication that the ML model 216 is sufficiently accurate, or a number of training rounds having taken place. The validation set 232 can include confirmed tissue states, tissue conditions, diagnoses, and/or combinations thereof. This allows the detected values (e.g., values discussed in connection with FIG. 9 or other values disclosed herein) to be validated using the validation sets 232. The validation sets 232 can be generated based on analysis to be performed.

Figure 3:
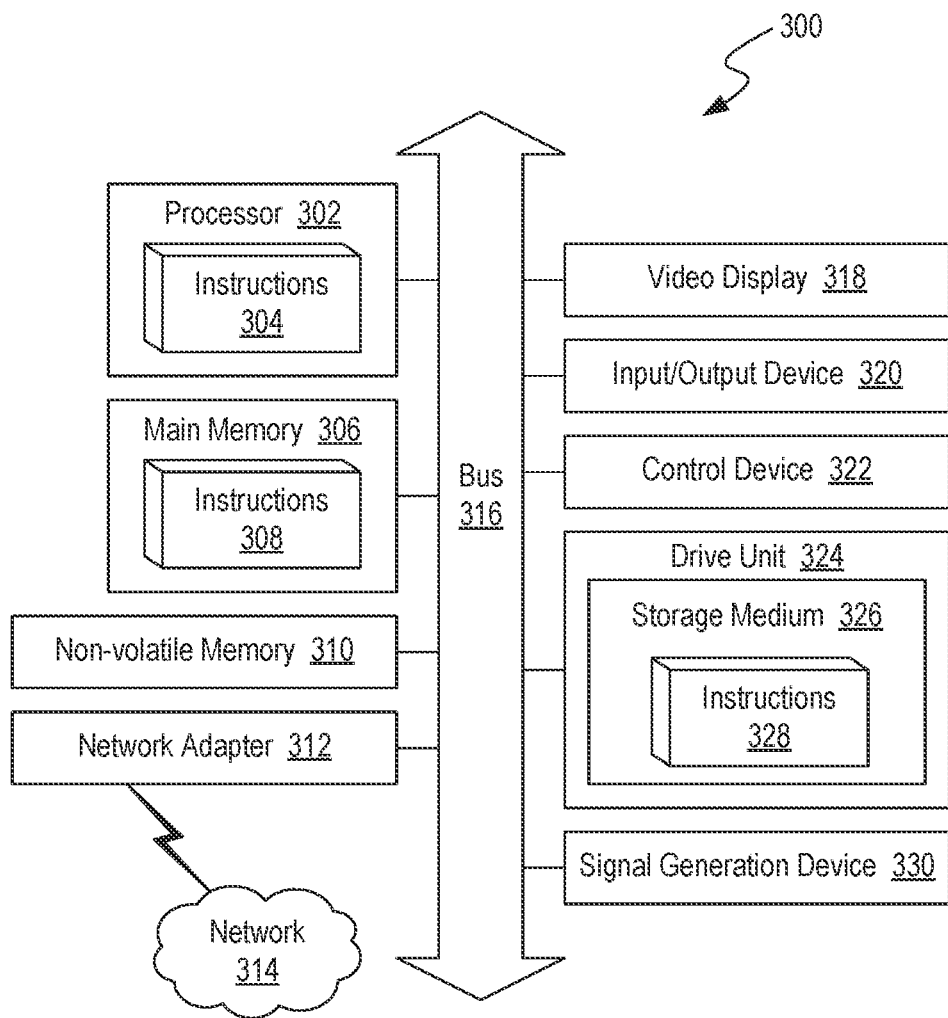
FIG. 3 is a block diagram illustrating an example computer system, in accordance with one or more embodiments.

FIG. 3 is a block diagram illustrating an example computer system, in accordance with one or more embodiments. Components of the example computer system 300 can be used to implement the monitors 112, the console 108, or the EHR database 106 illustrated and described in more detail with reference to FIG. 1. In some embodiments, components of the example computer system 300 are used to implement the ML system 200 illustrated and described in more detail with reference to FIG. 2. At least some operations described herein can be implemented on the computer system 300.

The computer system 300 can include one or more central processing units ("processors") 302, main memory 306, non-volatile memory 310, network adapters 312 (e.g., network interface), video displays 318, input/output devices 320, control devices 322 (e.g., keyboard and pointing devices), drive units 324 including a storage medium 326, and a signal generation device 320 that are communicatively connected to a bus 316. The bus 316 is illustrated as an abstraction that represents one or more physical buses and/or point-to-point connections that are connected by appropriate bridges, adapters, or controllers. The bus 316, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The computer system 300 can share a similar computer processor architecture as that of a desktop computer, tablet computer, personal digital assistant (PDA), mobile phone, game console, music player, wearable electronic device (e.g., a watch or fitness tracker), network-connected ("smart") device (e.g., a television or home assistant device), virtual/augmented reality systems (e.g., a head-mounted display), or another electronic device capable of executing a set of instructions (sequential or otherwise) that specify action(s) to be taken by the computer system 300.

While the main memory 306, non-volatile memory 310, and storage medium 326 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 328. The term "machine-readable medium" and "storage medium" shall also be taken to include any medium that is capable of storing, encoding, or carrying a set of instructions for execution by the computer system 300.

In general, the routines executed to implement the embodiments of the disclosure can be implemented as part of an operating system or a specific application, component, program, object, module, or sequence of instructions (collectively referred to as "computer programs"). The computer programs typically include one or more instructions (e.g., instructions 304, 308, 328) set at various times in various memory and storage devices in a computer device. When read and executed by the one or more processors 302, the instruction(s) cause the computer system 300 to perform operations to execute elements involving the various aspects of the disclosure.

Moreover, while embodiments have been described in the context of fully functioning computer devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 310, floppy and other removable disks, hard disk drives, optical discs (e.g., Compact Disc Read-Only Memory (CD-ROMS), Digital Versatile Discs (DVDs)), and transmission-type media such as digital and analog communication links.

The network adapter 312 enables the computer system 300 to mediate data in a network 314 with an entity that is external to the computer system 300 through any communication protocol supported by the computer system 300 and the external entity. The network adapter 312 can include a network adapter card, a wireless network interface card, a router, an access point, a wireless router, a switch, a multi-layer switch, a protocol converter, a gateway, a bridge, a bridge router, a hub, a digital media receiver, and/or a repeater.

The network adapter 312 can include a firewall that governs and/or manages permission to access proxy data in a computer network and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall can additionally manage and/or have access to an access control list that details permissions including the access and operation rights of an object by an individual, a machine, and/or an application, and the circumstances under which the permission rights stand.

Figure 4A:
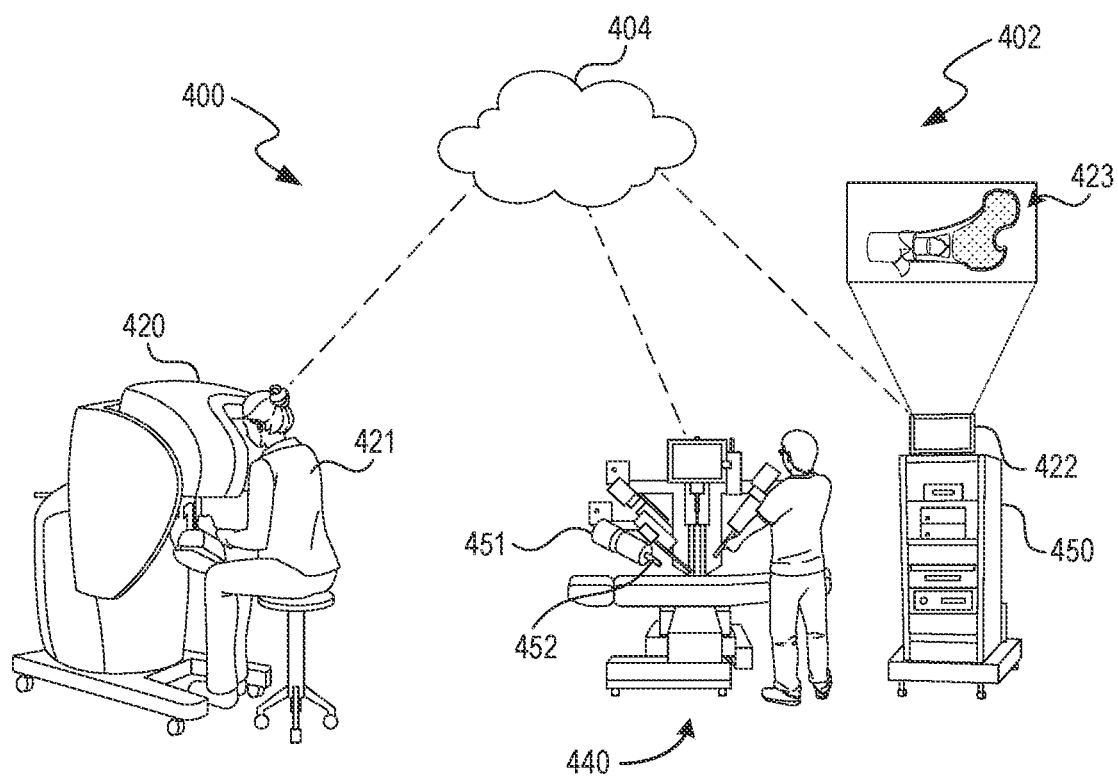
FIG. 4A is a block diagram illustrating an example robotic surgical system, in accordance with one or more embodiments.

FIG. 4A is a block diagram illustrating an example robotic surgical system 400, in accordance with one or more embodiments. The robotic surgical system 400 is the same as or similar to the robotic surgical system 160 illustrated and described in more detail with reference to FIG. 1. The robotic surgical system 400 can include components and features discussed in connection with FIGS. 1-3 and 4B-5. For example, the robotic surgical system 400 can include a console 420 with features of the console 108 of FIG. 1. Likewise, the components and features of FIG. 4A can be included or used with other embodiments disclosed herein. For example, the description of the input devices of FIG. 4A applies equally to other input devices (e.g., input devices 166 of FIG. 1).

The robotic surgical system 400 includes a user device or console 420 ("console 420"), a surgical robot 440, and a computer or data system 450. The console 420 can be operated by a surgeon and can communicate with components in an operating room 402, remote devices/servers, a network 404, or databases (e.g., database 106 of FIG. 1) via the network 404. The robotic surgical system 400 can include surgical control software and can include a guidance system (e.g., ML guidance system, AI guidance system, etc.), surgical planning software, event detection software, surgical tool software, etc. or other features disclosed herein to perform surgical step(s) or procedures or implement steps of processes discussed herein.

The user 421 can use the console 420 to view and control the surgical robot 440. The console 420 can be communicatively coupled to one or more components disclosed herein and can include input devices operated by one, two, or more users. The input devices can be hand-operated controls, but can alternatively, or in addition, include controls that can be operated by other parts of the user's body, such as, but not limited to, foot pedals. The console 420 can include a clutch pedal to allow the user 421 to disengage one or more sensor-actuator components from control by the surgical robot 440. The console 420 can also include display or output so that the one of more users can observe the patient being operated on, or the product being assembled, for example. In some embodiments, the display can show images, such as, but not limited to medical images, video, etc. For surgical applications, the images could include, but are not limited to, real-time optical images, real-time ultrasound, real-time OCT images and/or other modalities, or could include pre-operative images, such as MM, CT, PET, etc. The various imaging modalities can be selectable, programmed, superimposed, and/or can include other information superimposed in graphical and/or numerical or symbolic form.

The robotic surgical system 400 can include multiple consoles 420 to allow multiple users to simultaneously or sequentially perform portions of a surgical procedure. The term "simultaneous" herein refers to actions performed at the same time or in the same surgical step. The number and configuration of consoles 420 can be selected based on the surgical procedure to be performed, number and configurations of surgical robots, surgical team capabilities, or the like.

Figure 4B:
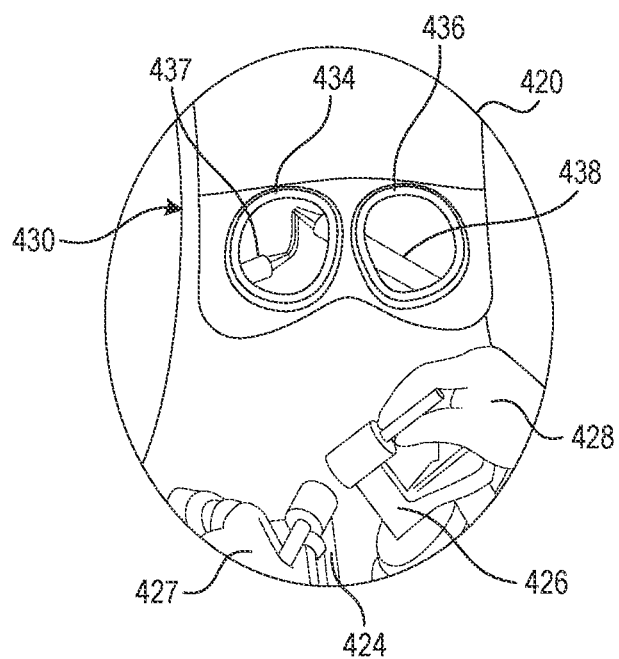
FIG. 4B illustrates an example console of the robotic surgical system of FIG. 4A, in accordance with one or more embodiments.

FIG. 4B illustrates an example console 420 of the robotic surgical system 400 of FIG. 4A, in accordance with one or more embodiments. The console 420 includes hand-operated input devices 424, 426, illustrated held by the user's left and right hands 427, 428, respectively. A viewer 430 includes left and right eye displays 434, 436. The user can view, for example, the surgical site, instruments 437, 438, or the like. The user's movements of the input devices 424, 426 can be translated in real-time to, for example, mimic the movement of the user on the viewer 430 and display (e.g., the high definition monitors 124 of FIG. 1) and within the patient's body while the user can be provided with output, such as alerts, notifications, and information. The information can include, without limitation, surgical or implantation plans, patient vitals, modification to surgical plans, values, scores, predictions, simulations, and other output, data, and information disclosed herein. The console 420 can be located at the surgical room or at a remote location.

The viewer 430 can display at least a portion of a surgical plan, including maps (e.g., tissue maps, bone tissue maps, tissue density maps, diseased tissue maps, tissue condition maps, etc.), past and future surgical steps, patient monitor readings (e.g., vitals), surgical room information (e.g., available team members, available surgical equipment, surgical robot status, or the like), images (e.g., pre-operative images, images from simulations, real-time images, instructional images, etc.), and other surgical assist information. In some embodiments, the viewer 430 can be a VR/AR headset, display, or the like. The robotic surgical system 400, illustrated and described in more detail with reference to FIG. 4A, can further include multiple viewers 430 so that multiple members of a surgical team can view the surgical procedure. The number and configuration of the viewers 430 can be selected based on the configuration and number of surgical robots.

Referring again to FIG. 4A, the surgical robot 440 can include one or more controllers, computers, sensors, arms, articulators, joints, links, grippers, motors, actuators, imaging systems, effector interfaces, end effectors, or the like. For example, a surgical robot with a high number of degrees of freedom can be used to perform complicated procedures whereas a surgical robot with a low number of degrees of freedom can be used to perform simple procedures. The configuration (e.g., number of arms, articulators, degrees of freedom, etc.) and functionality of the surgical robot 440 can be selected based on the procedures to be performed.

The surgical robot 440 can operate in different modes selected by a user, set by the surgical plan, and/or selected by the robotic surgical system 400. In some procedures, the surgical robot 440 can remain in the same mode throughout a surgical procedure. In other procedures, the surgical robot 440 can be switched between modes any number of times. The configuration, functionality, number of modes, and type of modes can be selected based on the desired functionality and user control of the robotic surgical system 400. The robotic surgical system 400 can switch between modes based on one or more features, such as triggers, notifications, warnings, events, etc. Different example modes are discussed below. A trigger can be implemented in software to execute a jump to a particular instruction or step of a program. A trigger can be implemented in hardware, e.g., by applying a pulse to a trigger circuit.

In a user control mode, a user 421 controls, via the console 420, movement of the surgical robot 440. The user's movements of the input devices can be translated in real-time into movement of end effectors 452 (one identified).

In a semi-autonomous mode, the user 421 controls selected steps and the surgical robot 440 autonomously performs other steps. For example, the user 421 can control one robotic arm to perform one surgical step while the surgical robot 440 autonomously controls one or more of the other arms to concurrently perform another surgical step. In another example, the user 421 can perform steps suitable for physician control. After completion, the surgical robot 440 can perform steps involving coordination between three or more robotic arms, thereby enabling complicated procedures. For example, the surgical robot 440 can perform steps involving four or five surgical arms, each with one or more end effectors 452.

In an autonomous mode, the surgical robot 440 can autonomously perform steps under the control of the data system 450. The robotic surgical system 400 can be pre-programmed with instructions for performing the steps autonomously. For example, command instructions can be generated based on a surgical plan. The surgical robot 440 autonomously performs steps or the entire procedure. The user 421 and surgical team can observe the surgical procedure to modify or stop the procedure. Advantageously, complicated procedures can be autonomously performed without user intervention to enable the surgical team to focus and attend to other tasks. Although the robotic surgical system 400 can autonomously perform steps, the surgical team can provide information in real-time that is used to continue the surgical procedure. The information can include physician input, surgical team observations, and other data input.

The robotic surgical system 400 can also adapt to the user control to facilitate completion of the surgical procedure. In some embodiments, the robotic surgical system 400 can monitor, via one or more sensors, at least a portion of the surgical procedure performed by the surgical robot 440. The robotic surgical system 400 can identify an event, such as a potential adverse surgical event, associated with a robotically performed surgical task. For example, a potential adverse surgical event can be determined based on acquired monitoring data and information for the end effector, such as surgical tool data from a medical device report, database, manufacturer, etc. The robotic surgical system 400 can perform one or more actions based on the identified event. The actions can include, without limitation, modification of the surgical plan to address the potential adverse surgical event, thereby reducing the risk of the event occurring. The adverse surgical event can include one or more operating parameters approaching respective critical thresholds, as discussed in connection with FIG. 12. The adverse surgical events can be identified using a machine learning model trained using, for example, prior patient data, training sets (e.g., tool data), etc.

In some embodiments, the robotic surgical system 400 determines whether a detected event (e.g., operational parameters outside a target range or exceeding a threshold, etc.) is potentially an adverse surgical event based on one or more criteria set by the robotic surgical system 400, user, or both. The adverse surgical event can be an adverse physiological event of the patient, surgical robotic malfunction, surgical errors, or other event that can adversely affect the patient or the outcome of the surgery. Surgical events can be defined and inputted by the user, surgical team, healthcare provider, manufacturer of the robotic surgery system, or the like.

The robotic surgical system 400 can take other actions in response to identification of an event. If the robotic surgical system 400 identifies an end effector malfunction or error, the robotic surgical system 400 can stop usage of the end effector and replace the malfunctioning component (e.g., surgical tool or equipment) to complete the procedure. The robotic surgical system 400 can monitor hospital inventory, available resources in the surgical room 402, time to acquire equipment (e.g., time to acquire replacement end effectors, surgical tools, or other equipment), and other information to determine how to proceed with surgery. The robotic surgical system 400 can generate multiple proposed surgical plans for continuing with the surgical procedure. The user and surgical team can review the proposed surgical plans to select an appropriate surgical plan. The robotic surgical system 400 can modify a surgical plan with one or more corrective surgical steps based on identified surgical complications, sensor readings, or the like.

The robotic surgical system 400 can retrieve surgical system information from a database to identify events. The database can describe, for example, maintenance of the robotic surgery system, specifications of the robotic surgery system, specifications of end effectors, surgical procedure information for surgical tools, consumable information associated with surgical tools, operational programs and parameters for surgical tools, monitoring protocols for surgical tools, or the like. The robotic surgical system 400 can use other information in databases disclosed herein to generate rules for triggering actions, identifying warnings, defining events, or the like. Databases can be updated with data (e.g., intraoperative data collected during the surgical procedure, simulation data, etc.) to intraoperatively adjust surgical plans, collect data for ML/AI training sets, or the like. Data from on-site and off-site simulations (e.g., pre-, or post-operative virtual simulations, simulations using models, etc.) can be generated and collected.

The surgical robot 440 can include robotic arms 451 (one identified) with integrated or removable end effectors 452 (one identified). The end effectors 452 can include, without limitation, bone mapper devices, imagers (e.g., cameras, optical guides, etc.), robotic grippers, instrument holders, cutting instruments (e.g., cutters, scalpels, or the like), drills, cannulas, reamers, rongeurs, scissors, clamps, or other equipment or surgical tools disclosed herein. In some embodiments, the end effectors can be reusable or disposable surgical tools. The number and configuration of end effectors can be selected based on the configuration of the robotic system, procedure to be performed, surgical plan, etc. Imaging and viewing technologies can integrate with the surgical robot 440 to provide more intelligent and intuitive results.

The data system 450 can improve surgical planning, monitoring (e.g., via the display 422), data collection, surgical robotics/navigation systems, intelligence for selecting instruments, implants, etc. The data system 450 can execute, for example, surgical control instructions or programs for a guidance system (e.g., ML guidance system, AI guidance system, etc.), surgical planning programs, event detection programs, surgical tool programs, etc. For example, the data system 450 can increase procedure efficiency and reduce surgery duration by providing information insertion paths, surgical steps, or the like. The data system 450 can be incorporated into or include other components and systems disclosed herein. The display 422 can display, for example, a diagnosis of tissue, maps, surgical plans, etc. For example, the display 422 can display a diagnostic map showing, for example, a bone 423 (discussed in more detail below with respect to FIG. 10), regions of interest (e.g., zones of diseased tissue, regions of tissue with specific characteristic(s), margins, etc.), features of interest, anatomical elements (e.g., cartilage, soft tissue, etc.), or the like. In some embodiments, the diagnostic map can include tissue density, tissue state, identified disease tissue, or the like. The system 402 can use the displayed data to perform one or more surgical steps. A user can view the display 422 to confirm the position of the tissue during the procedure.

The robotic surgical system 400 can be used to perform open procedures, minimally invasive procedures, such as laparoscopic surgeries, non-robotic laparoscopic/abdominal surgery, retroperitoneoscopy, arthroscopy, pelviscopy, nephroscopy, cystoscopy, cisternoscopy, sinoscopy, hysteroscopy, urethroscopy, and the like. The methods, components, apparatuses, and systems can be used with many different systems for conducting robotic or minimally invasive surgery. One example of a surgical system and surgical robots which can incorporate methods and technology is the DAVINCI™ system available from Intuitive Surgical, Inc.™ of Mountain View, Calif. However, other surgical systems, robots, and apparatuses can be used.

The robotic surgical system 400 can perform one or more simulations using selected entry port placements and/or robot positions, to allow a surgeon or other user to practice procedures. The practice session can be used to generate, modified, or select a surgical plan. In some embodiments, the system can generate a set of surgical plans for physician consideration. The physician can perform practice sessions for each surgical plan to determine and select a surgical plan to be implemented. In some embodiments, the systems disclosed herein can perform virtual surgeries to recommend a surgical plan. The physician can review the virtual simulations to accept or reject the recommended surgical plan. The physician can modify surgical plans pre-operative or intraoperatively.

Embodiments can provide a means for mapping the surgical path for neurosurgery procedures that minimize damage through artificial intelligence mapping. The software for artificial intelligence is trained to track the least destructive pathway. The physician can make an initial incision based on a laser marking on the skin that illuminates the optimal site. Next, a robot can make a small hole and insert surgical equipment (e.g., guide wires, cannulas, etc.) that highlights the best pathway. This pathway minimizes the amount of tissue damage that occurs during surgery. Mapping can also be used to identify one or more insertion points associated with a surgical path. Mapping can be performed before treatment, during treatment, and/or after treatment. For example, pretreatment and posttreatment mapping can be compared by the surgeon and/or ML/AI system. The comparison can be used to determine next steps in a procedure and/or further train the ML/AI system.

Figure 5:
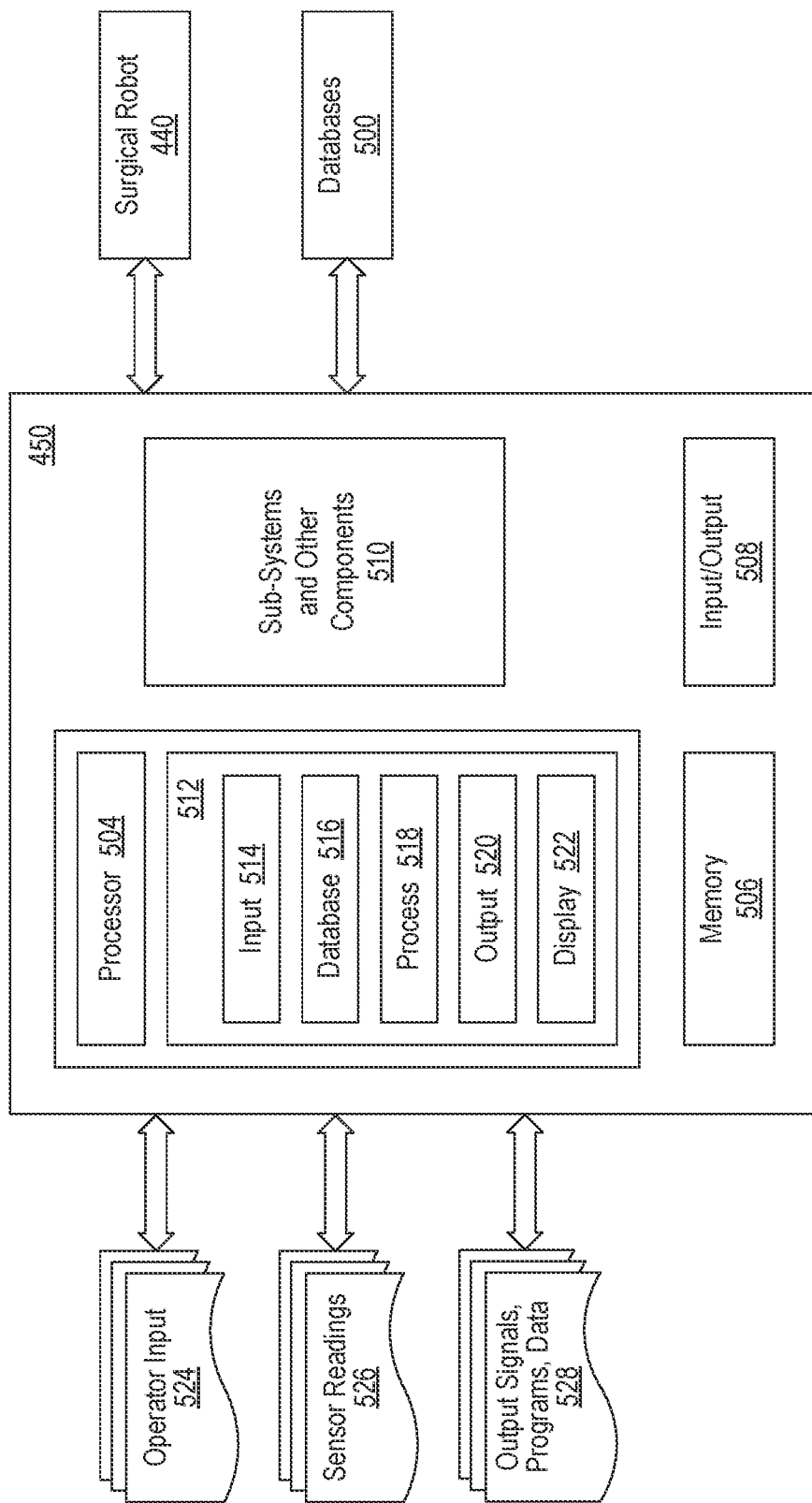
FIG. 5 is a schematic block diagram illustrating subcomponents of the robotic surgical system of FIG. 4A, in accordance with one or more embodiments.

FIG. 5 is a schematic block diagram illustrating subcomponents of the robotic surgical system 400 of FIG. 4A in accordance with embodiment of the present technology. The data system 450 has one or more processors 504, a memory 506, input/output devices 508, and/or subsystems and other components 510. The processor 504 can perform any of a wide variety of computing processing, image processing, robotic system control, plan generation or modification, and/or other functions. Components of the data system 450 can be housed in a single unit (e.g., within a hospital or surgical room) or distributed over multiple, interconnected units (e.g., though a communications network). The components of the data system 450 can accordingly include local and/or devices.

As illustrated in FIG. 5, the processor 504 can include a plurality of functional modules 512, such as software modules, for execution by the processor 504. The various implementations of source code (i.e., in a conventional programming language) can be stored on a computer-readable storage medium or can be embodied on a transmission medium in a carrier wave. The modules 512 of the processor 504 can include an input module 514, a database module 516, a process module 518, an output module 520, and, optionally, a display module 524 for controlling the display.

In operation, the input module 514 accepts an operator input 524 via the one or more input devices, and communicates the accepted information or selections to other components for further processing. The database module 516 organizes plans (e.g., robotic control plans, surgical plans, etc.), records (e.g., maintenance records, patient records, historical treatment data, etc.), surgical equipment data (e.g., instrument specifications), control programs, and operating records and other operator activities, and facilitates storing and retrieving of these records to and from a data storage device (e.g., internal memory 506, external databases, etc.). Any type of database organization can be utilized, including a flat file system, hierarchical database, relational database, distributed database, etc.

In the illustrated example, the process module 518 can generate control variables based on sensor readings 526 from sensors (e.g., end effector sensors of the surgical robot 440, bone mapper devices, patient monitoring equipment, etc.), operator input 524 (e.g., input from the surgeon console 420 and/or other data sources), and the output module 520 can communicate operator input to external computing devices and control variables to controllers. The display module 522 can be configured to convert and transmit processing parameters, sensor readings 526, output signals 528, input data, treatment profiles and prescribed operational parameters through one or more connected display devices, such as a display screen, touchscreen, printer, speaker system, etc.

In various embodiments, the processor 504 can be a standard central processing unit or a secure processor. Secure processors can be special-purpose processors (e.g., reduced instruction set processor) that can withstand sophisticated attacks that attempt to extract data or programming logic. The secure processors cannot have debugging pins that enable an external debugger to monitor the secure processor's execution or registers. In other embodiments, the system can employ a secure field-programmable gate array, a smartcard, or other secure devices.

The memory 506 can be standard memory, secure memory, or a combination of both memory types. By employing a secure processor and/or secure memory, the system can ensure that data and instructions are both highly secure and sensitive operations such as decryption are shielded from observation. In various embodiments, the memory 506 can be flash memory, secure serial EEPROM, secure field-programmable gate array, or secure application-specific integrated circuit. The memory 506 can store instructions for causing the surgical robot 440 to perform acts disclosed herein.

The input/output device 508 can include, without limitation, a touchscreen, a keyboard, a mouse, a stylus, a push button, a switch, a potentiometer, a scanner, an audio component such as a microphone, or any other device suitable for accepting user input and can also include one or more video monitors, a medium reader, an audio device such as a speaker, any combination thereof, and any other device or devices suitable for providing user feedback. For example, if an applicator moves an undesirable amount during a treatment session, the input/output device 508 can alert the subject and/or operator via an audible alarm. The input/output device 508 can be a touch screen that functions as both an input device and an output device.

The data system 450 can output instructions to command the surgical robot 440 and communicate with one or more databases 2600. The surgical robot 440 or other components disclosed herein can communicate to send collected data (e.g., sensor readings, instrument data, surgical robot data, etc.) to the database 500. This information can be used to, for example, create new training data sets, generate plans, perform future simulations, post-operatively analyze surgical procedures, or the like. The data system 450 can be incorporated, used with, or otherwise interact with other databases, systems, and components disclosed herein. In some embodiments, the data system 450 can be incorporated into the surgical robot 440 or other systems disclosed herein. In some embodiments, the data system 450 can be located at a remote location and can communicate with a surgical robot via one or more networks. For example, the data system 450 can communicate with a hospital via a network, such as a wide area network, a cellular network, etc. One or more local networks at the hospital can establish communication channels between surgical equipment within the surgical room.

A surgical program or plan ("surgical plan") can include, without limitation, patient data (e.g., pre-operative images, medical history, physician notes, etc.), imaging programs, surgical steps, mode switching programs, criteria, goals, or the like. The imaging programs can include, without limitation, AR/VR programs, identification programs (e.g., fiducial identification programs, tissue identification programs, target tissue identification programs, etc.), image analysis programs, or the like. Surgical programs can define surgical procedures or a portion thereof. For example, surgical programs can include end effector information, positional information, surgical procedure protocols, safety settings, surgical robot information (e.g., specifications, usage history, maintenance records, performance ratings, etc.), order of surgical steps, acts for a surgical step, feedback (e.g., haptic feedback, audible feedback, etc.), or the like. The mode switching programs can be used to determine when to switch the mode of operation of the surgical robot 440. For example, mode switching programs can include threshold or configuration settings for determining when to switch the mode of operation of the surgical robot 440. Example criteria can include, without limitation, thresholds for identifying events, data for evaluating surgical steps, monitoring criteria, patient health criteria, physician preference, or the like. The goals can include intraoperative goals, post-operative goals (e.g., target outcomes, metrics, etc.), goal rankings, etc. Monitoring equipment or the surgical team can determine goal progress, whether a goal has been achieved, etc. If an intraoperative goal is not met, the surgical plan can be modified in real-time so that, for example, the post-operative goal is achieved. The post-operative goal can be redefined intraoperatively in response to events, such as surgical complications, unplanned changes to patient's vitals, etc.

The surgical plan can also include healthcare information, surgical team information, assignments for surgical team members, or the like. The healthcare information can include surgical room resources, hospital resources (e.g., blood banks, standby services, available specialists, etc.), local or remote consultant availability, insurance information, cost information (e.g., surgical room costs, surgical team costs, etc.).

The systems disclosed herein can generate pre-operative plans and simulation plans. Pre-operative plans can include scheduling of equipment, surgical room, staff, surgical teams, and resources for surgery. The systems can retrieve information from one or more databases to generate the pre-operative plan based on physician input, insurance information, regulatory information, reimbursements, patient medical history, patient data, or the like. Pre-operative plans can be used to generate surgical plans, cost estimates, scheduling of consultants and remote resources, or the like. For example, a surgical plan can be generated based on available resources scheduled by the pre-operative plans. If a resource becomes unavailable, the surgical plan can be adjusted for the change in resources. The healthcare provider can be alerted if additional resources are recommended. The systems disclosed herein can generate simulation plans for practicing surgical procedures. On approval, a surgeon can virtually simulate a procedure using a console or another simulation device. Plans (e.g., surgical plans, implantation plans, etc.) can be generated and modified based on the surgeon's performance and simulated outcome.

The systems disclosed herein can generate post-operative plans for evaluating surgical outcomes, developing physical therapy and/or rehab programs and plans, etc. The post-operative plans can be modified by the surgical team, primary care provider, and others based on the recovery of the patient. In some embodiments, systems generate pre-operative plans, surgical plans, and post-operative plans prior to beginning a surgical procedure. The system then modifies one or more or the plans as additional information is provided. For example, one or more steps of the methods discussed herein can generate data that is incorporated into the plan. ML data sets to be incorporated into the plan generate a wide range of variables to be considered when generating plans. Plans can be generated to optimize patient outcome, reduce or limit the risk of surgical complications, mitigate adverse events, manage costs for surgical procedures, reduce recovery time, or the like. The healthcare provider can modify how plans are generated over time to further optimize based on one or more criteria.

Figure 6:
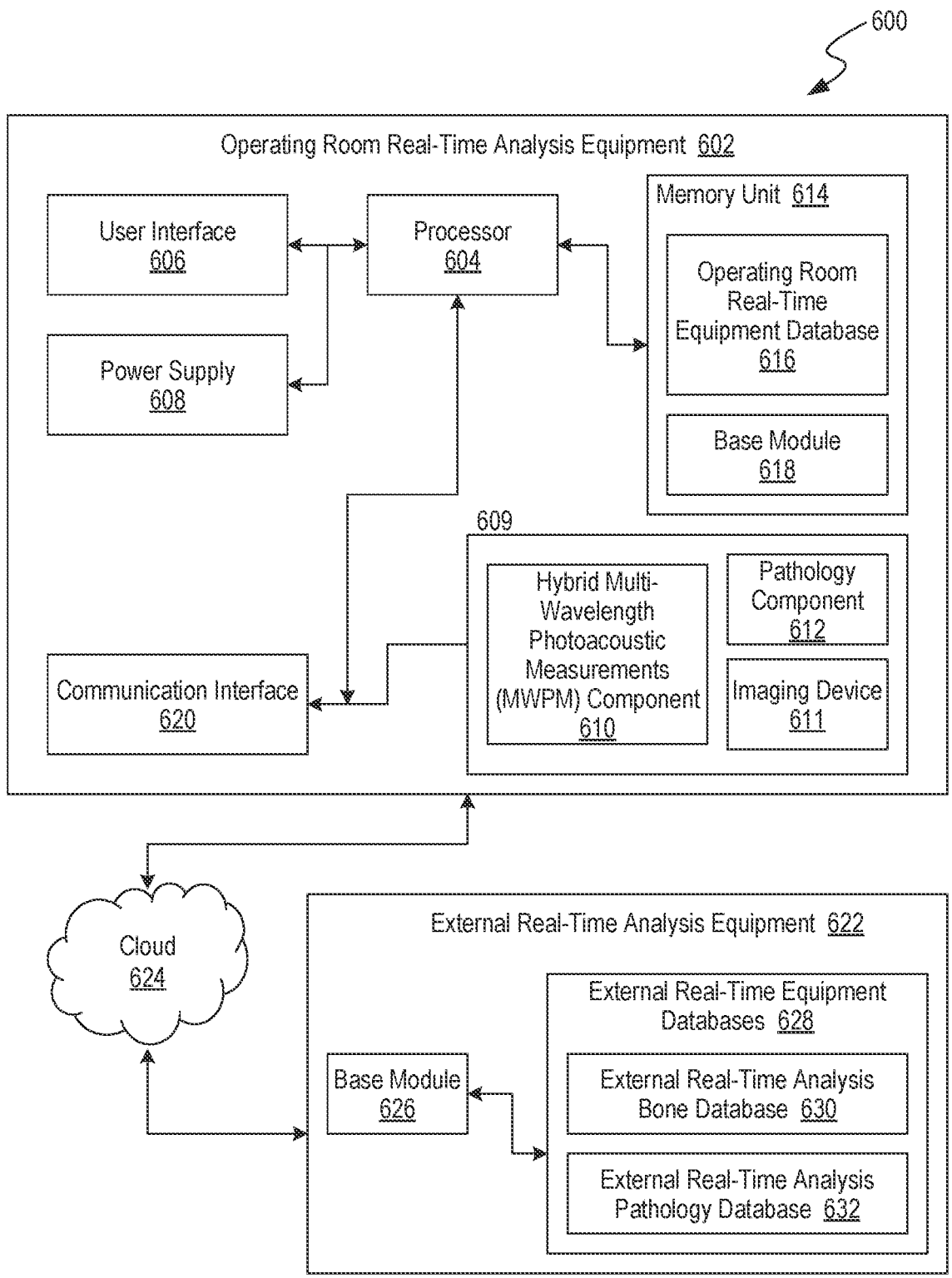
FIG. 6 is a block diagram of a system for performing real-time analysis of bone tissue in accordance with some embodiments of the present technology.

FIG. 6 is a block diagram of a system 600 for performing real-time analysis of bone tissue in accordance with some embodiments of the present technology. The system 600 can be incorporated into or used with technology discussed in connection with FIGS. 1-5. For example, one or more components of the analysis equipment 602 can be incorporated into the operating room 102 discussed in FIG. 1. By way of another example, the user interface 606 of the system 600 can be part of the interface 420 discussed in connection with FIG. 4B. Output from the system 600 can be transmitted to the controller 450 at FIG. 5 and/or various other components disclosed herein. Accordingly, the system 600 can be incorporated into robotic surgery systems, or utilized to perform manual procedures or to perform other procedures disclosed herein.

In some embodiments, the system 600 is configured to perform in-situ testing and analysis of samples of a target tissue (e.g., bone tissue, scar tissue, pathogenic tissue, and/or other suitable bodily tissue). Additionally, or alternatively, the system 600 can perform in-situ testing and analysis of surrounding tissues without requiring a biopsy or bone sample to be taken or removed from a patient. To do so, for example, the system 600 can include a sampling unit capable of sampling bone tissue in real-time by subjecting the target tissue and/or surrounding tissue (also referred to collectively herein as the "tissue sample") to at least one test. The test(s) can include multi-wavelength photoacoustic measurements (MWPM), ultrasound measurements, one or more x-ray measurements, other optical measurements, one or more targeted ultrasound measurements, and/or various other suitable measurements. In some embodiments, the system 600 performs one or more multimodality analyses in which one or more multi-sensing devices perform (sequentially or concurrently) a plurality of tests, such as optical tests, acoustic tests, photoacoustic tests, combinations thereof, or the like. The tests can be performed during one or more scans of the tissue sample. In a single scan test, the system 600 can concurrently perform multiple tests while moving along the tissue sample. In multiple scan test, the system 600 can sequentially perform tests during corresponding scans and/or can concurrently perform multiple tests during each scan. The system 600 can perform different imaging or scanning protocols based on the analysis to be performed.

The system 600 can then facilitate communication with a robotic surgical system, doctor, surgeon, or other medical professional by providing results (e.g., multiplexed data, raw data, visualizations of the data, and the like) from the test(s) in real-time. Further, the system 600 can combine the results from the test(s) (sometimes referred to herein as the "scan") to provide a diagnosis of the tissue sample. In surgical procedures, the results can be automatically transmitted to a robotic surgical system that analyses the results to perform one or more surgical steps. The robotic surgical system can request additional information from the system 600 to, for example, complete a surgical step, confirm completion of a surgical step, plan a surgical step, plan a series of surgical steps, or the like. For example, the surgical system 402 at FIG. 4A can receive results from the system 600 to perform a MWPM-guided robotic surgical step. In some embodiments, the results can be displayed via display 422 for viewing by the surgical team. Additionally, or alternatively, the results can be viewable via console 420 by a user 421 while, for example, monitoring or performing one or more surgical steps.

As discussed in more detail below, the system 600 can perform various measurements to obtain a tissue density value (e.g., a bone mineral density (BMD) value), a MWMP value, a µ3 value, one or more x-ray images, CT scan values, and/or any other suitable values during the scan (sometimes referred to collectively as "values from the scan"), then identify relevant reference cases in a database (third party or local). The system 600 can then generate the diagnosis based on the values from the scan, predetermined threshold values for each of the measured values, and/or the diagnoses in the identified reference cases. Additionally, or alternatively, the system 600 can generate a 3D analysis of the tissue sample using the values from the scan and create a map (e.g., a visualization similar to a detailed 3D x-ray from medical imagery) of the tissue sample. The 3D analysis can include a variety of tissue analytics generated using a tissue mapper device, automatically generated diagnostic information and/or suggested diagnoses, and the like. The system 600 can then provide the doctor (or other medical professional) with access to the map to provide a diagnosis and/or medical recommendations based on the map.

As illustrated in FIG. 6, the system 600 can include operating room real-time analysis equipment component 602 (sometimes referred to herein as the "operating room 602") that is configured to perform real-time testing and analysis of the tissue sample of the patient. In various embodiments, the target tissue can include, but not be limited to, bone tissue for detection of osteoporosis, osteopenia, bone cancer, and the like; and/or pathogenic tissue for detection of osteomyelitis, other cancerous cells, inflammation, and the like. In the illustrated embodiment, the operating room 602 includes a processor 604 configured to perform a plurality of functions related to the operating room 602, as well as a user interface 606, a power supply 608, a tissue mapper device such as bone mapper device 609, a pathology component 612, a memory unit 614, and a communication interface 620 all operatively coupled to the processor 604. The bone mapper device 609 can include one or more hybrid imaging components, here a hybrid MWPM component 610, and imaging devices 611. In some embodiments, the operating room 602 includes the features discussed in connection with FIGS. 1-5.

The processor 604 can be configured to perform a plurality of functions related to the operating room 602, for example, based on a set of instructions and/or received inputs. In various embodiments, the functions can include commanding the hybrid MWMP component 610 and/or the pathology component 612 to perform measurements to generate sample data, receiving the sample data, retrieving previous sample data relevant to an individual patient, retrieving previous sample data related to one or more reference cases, evaluating the sample data, generating the 3D map based one the sample data, and the like. In some embodiments, the set of instructions is stored in the memory unit 614. In some embodiments, the set of instructions causes the processor 604 to automatically perform one or more scans over and/or an analysis of the tissue sample using any of the components of the operating room 602.

The user interface 606 can display the results of the scan(s) (e.g., measurements taken using the hybrid MWMP component 610, the diagnosis of the tissue sample, the 3D map, and the like) for the doctor, surgeon, and/or other medical professional. In some embodiments, the operating room 602 includes a second user interface (not shown, sometimes also referred to herein as an "auxiliary interface") coupled to an imaging device (not shown) that is directed at the tissue sample. The second user interface can continuously display actions performed during testing and analysis of the tissue sample. In various such embodiments, the imaging device can include a camera, a video recorder, an optical image sensor, and the like. In some embodiments, the imaging device is directed toward the tissue sample to capture a real-time image which can be fed to the auxiliary user interface for the surgeon to analyze the target tissue and surrounding tissues while the hybrid MWMP component 610 scans the tissue sample (e.g., takes measurements of the tissue sample). In some embodiments, the auxiliary user interface allows the doctor to provide instructions to the processor 604 during the scan to control one or more components of the operating room 602.

The power supply 608 can be operatively coupled to the processor 604 and/or any other component of the operating room 602 to drive each of the components. In some embodiments, the power supply 608 is an internal power source for the operating room 602. Purely by way of example, the power supply 608 can include a battery. In a specific, non-limiting example, the power supply 608 can include a Lithium polymer battery (Li—Po), due to its lightweight, high discharge rate, and relatively high capacity. In another example, the power supply 608 can include a wall outlet (or other suitable component) coupled to an external power source.

As illustrated in FIG. 6, the processor 604 can be communicatively coupled to the hybrid MWPM component 610 (e.g., via the communication interface 620 and/or any other suitable component) to direct the hybrid MWPM component 610 to perform actions related to the analysis of the tissue sample. For example, the processor 604 can direct the hybrid MWPM component 610 to perform a scan of the tissue sample. During the scan, the hybrid MWPM component 610, discussed in more detail below with respect to FIG. 7, can impart ultrasonic and/or photoacoustic waves through the tissue sample and measure a response. As a result, the hybrid MWPM component 610 can determine a variety of values, such as a material density value (e.g., a value for bone material density (BMD)), an absorption spectrum (e.g., $\mu_a$) value, and/or a MWPM value for one or more portions of the tissue sample (sometimes referred to collectively herein). The pathology component 612, in conjunction with the processor 604, can then provide a pathology analysis of the data collected by the hybrid MWPM component 610. Purely by way of example, the pathology component 612 and the processor 604 can identify a bone condition in the tissue sample, such as osteoporosis, clinical osteopenia, cancerous bone, normal bone, and/or any other condition. Because the system 600 diagnoses the tissue sample based on a variety of values from the scan, the system is able to generate an accurate, real-time diagnosis of the tissue sample without requiring exposure to potentially harmful levels of radiation.

Additionally, or alternatively, the hybrid MWPM component 610 and/or the processor 604 can create the 3D map (or other visualization) of the tissue sample using images (e.g., still images, video, topology mapping, etc.) from the imaging device(s) 611, the values from the scan, and/or any other associated imagery (e.g., images from the imaging component external to the bone mapper device 609). As discussed above, the processor 604 can then display the 3D map (e.g., on the user interface 606) for review by a doctor or other medical professional. In some embodiments, image data captured by the imaging device 611 are used to generate a 3D map of the sample tissue. Output from the hybrid MWPM component 610 can be overlaid onto the image data. For example, the captured image can be a color still image and the output of the hybrid MWPM component 610 can be colored to provide a false clear image. The MWPM output can be readily identifiable by a user. This allows a user to see overlaid output or analytics generated from the hybrid MWPM component 610. In some procedures, the imaging device 611 can scan the tissue sample to generate a 3D image of the tissue sample. The output from the hybrid MWPM component 610 can be overlaid onto the scan based on the known positional information between the component 610 and the imaging device 611. This allows the acoustic-generated image data to be keyed to the image data from the imaging device 611. Additionally, or alternatively, the processor 604 can display the diagnosis generated by the system 600 and/or the values from the scan. The doctor can then diagnose the tissue sample based on the displayed information. Because the system 600 is able to generate a 3D map and/or a variety of values from the scan, the system 600 can help improve the accuracy of the doctors' real-time diagnosis without requiring exposure to potentially harmful levels of radiation. Purely by way of example, by including values from both ultrasound and photoacoustic measurements, the system 600 can create an accurate 3D map of an imaged bone that allows the doctor to assess both density of the bone, amount of bone material, and matrix structure of the bone. In a specific, non-limiting example, if one of the values from the scan is above (or below) a predetermined threshold, the system 600 can set an initial diagnosis for review by the doctor. In various embodiments, the predetermined threshold can be set by the system 600 based on a plurality of reference cases (e.g., when a consistent threshold emerges), input by the doctor based on a practice preference, and/or retrieved from a third party (e.g., another medical database, a trusted medical publication, and the like).

The memory unit 614 can store real-time data acquired from the patient (e.g., values from the scan, related medical data, other surgical data, patient history, and the like). For example, in the illustrated embodiment, the memory unit 614 includes an operating room real-time equipment database 616 ("database 616") that can store real-time data acquired from the patient undergoing testing (e.g., bone testing) and/or any related analyses. In various embodiments, the real-time data can include the date of operation, surgery, and/or tests (sometimes referred to collectively herein as a "medical procedure" and/or a "surgical operation"); doctor identification and specialty; patient identification and background medical information; tissue density values (e.g., BMD values), MWPM values, $\mu_a$ values, and/or any other suitable values for diagnosis of tissue; data associated with a diagnosis and/or analysis; and/or metadata associated with the diagnosis and/or analysis. Additionally, or alternatively, the database 616 can store information related to the physical location and/or orientation of the components of the system 600; a mapping analysis of the measurements to the tissue sample (e.g., information related to a picture location on the tissue sample); and the like. In a specific, non-limiting example, the database 616 can store information showing that a patient named John Doe is having bone surgery on 21 Jun. 2020; the surgery is to be performed by Dr. Smith at a surgical facility in Paris; that a sample bone (e.g., the ulna) is selected to be monitored for diagnosis of osteoporosis using the hybrid MWPM component 610; that scans by the hybrid MWPM component 610 measured a BMD value of −1.8, an MWPM value of 780 nm, and a $\mu_a$ value of 2; that the predetermined threshold MWPM value for John Doe was set at 750 nm; and that Dr. Smith provided a diagnosis that John Doe is suffering from osteoporosis based on the values from the scan. In another specific example, the database 616 can store information that the imaging device, when directed towards the ulna bone (e.g., the target tissue) of John Doe, indicated a porous structure all over the ulna. Osteoporosis may be indicated by a $\mu_a$ between 1 and 2 with a deviation of up to 0.5 at an MWPM between 700 nm and 950 nm which correlates to a BMD value of less than −2.5, also known as a T-value. A BMD below −1 may indicate a low bone density. This would correlate to a CT scan of a bone with a bone density represented by less than 135 Hounsfield Units (HUs). In some embodiments, the presence of the porous bone structure can help confirm the BMD value of −1.8 from the hybrid MWPM component 610.

In some embodiments, the memory unit 614 is operably coupled to the processor 604 to store and retrieve historical data and/or reference data (e.g., medical data related to one or more reference cases) in real-time. Purely by way of example, as real-time scan values are gathered by the hybrid MWPM component 610, the memory unit 614 can retrieve reference cases from a third-party database with similar scan values (e.g., comparable BMD, MWPM, and/or $\mu_a$ values).

In the illustrated embodiment, memory unit 614 also includes a base module 618 that, stores, receives, and/or retrieves information related to the medical procedure. The information can include instructions that, when executed in conjunction with the processor 604, cause the base module 618 to control components of the operating room 602 in real-time to obtain relevant measurements. Purely by way of example, the instructions can cause the base module 618 control the hybrid MWPM component 610 and/or perform actions related to testing and analysis (e.g., to perform a scan of the tissue sample, filter raw data received from the scan, analyze values from the scan, and the like). In some embodiments, the instructions cause the base module 618 to perform the scan with the hybrid MWPM component 610 repeatedly during a time frame and/or to repeat the scan after a predetermined time period. In some embodiments, the base module 618 includes a plurality of sub-modules. In various such embodiments, the plurality of sub-modules include an initiation module configured to initiate the system 600; a polling module configured to turn on and/or calibrate the hybrid MWPM component 610; an analysis module configured to identify correlations between values from the scan and one or more reference cases, then identify a suitable reference case based on the correlations; a mapping module configured to map the values from the scan with the hybrid MWPM component 610 with the imaging device data; and/or a communication module configured to send raw data, processed data, and/or the results from analyses to the database 616. Additional details on the functionality of the base module 618, in accordance with some embodiments of the present technology, are described below with reference to FIGS. 8A and 8B.

In some embodiments, the operating room 602 and/or components thereof utilize artificial intelligence (AI) and/or Machine learning (ML) to analyze the values from the scan, provide recommendations for the scan, and identify correlations between the data received from the hybrid MWPM component 610 and the imaging device. Purely by way of example, the AI/ML can analyze the values from the scan (e.g., the raw data from the hybrid MWPM component 610), to provide recommendations related to the procedure and/or tests of the tissue sample (e.g., to rescan a portion of the tissue sample, to scan an additional portion of the bone, and the like). In another example, the AI/ML can identify correlations between various types of data to create a function to predict future events and/or measurements in the surgical procedure. For example, when the hybrid MWPM component 610 is directed toward a bone tissue and generates a light beam with energy per laser pulse in a range between 15 mJ/cm$^2$ to 20 mJ/cm$^2$, and a beam splitter divides the light beam in a 1:9 ratio, with a diameter of the light beam as 4 mm, and the values from the scan indicate a relative bone material density (BMD) value of 2.5 with a multi-wavelength photoacoustic measurement (MWPM) of 750 nm and a $\mu_a$ value of 2, the AI/ML data can predict the values that will be obtained in scans of other tissue on the patient. Additionally, or alternatively, the AI/ML can identify reference cases with similar tissue compositions based on the values from the scan, imagery of the tissue sample, and/or other information received from the hybrid MWPM component 610 (e.g., operational parameters during the scan). By generating correlations using the AI/ML component, the operating room 602 (and components thereof) can identify previously unrecognized trends, increase the accuracy of the reference cases identified, and increase the accuracy of diagnoses of the tissue sample.

As further illustrated in FIG. 6, the system 600 can include external real-time analysis equipment 622 ("external equipment 622," such as off-premise equipment, third party equipment, and the like) that is communicatively coupled to the operating room 602 via a cloud network 624. For example, the communication interface 620 can be communicatively coupled to the cloud network 624 to facilitate communication from the operating room 602 to the external equipment 622. In some embodiments, the communication interface 620 includes a radio communication or other wired or wireless communication. In some embodiments, the communication interface 620 includes a wired and/or a wireless network connection. The communication interface 620, if wireless, may be implemented using communication techniques such as Visible Light Communication (VLC), Worldwide Interoperability for Microwave Access (WiMAX), Long Term Evolution (LTE), Wireless Local Area Network (WLAN), Infrared (IR) communication, Public Switched Telephone Network (PSTN), Radio waves, and other communication techniques, known in the art.

In some embodiments, the external equipment 622 communicates with the communication interface 620 to provide one or more services to the operating room 602. For example, the external equipment 622 can communicate with the operating room 602 to store the real-time data, provide data for potential reference cases, and/or to perform any of the analyses discussed above. To do so, the external equipment 622 can include a base module 626 configured to perform operations in a similar manner as the base module 618 of the operating room 602. Further, the external equipment 622 can include an external real-time equipment database 628 ("database 628") configured to update the database 616 via the cloud network 624 periodically and/or constantly. In various embodiments, the database 628 can be divided into various sub-databases to store different information related to the patient, such as medical records for each patient in the reference cases (e.g., previous surgeries, operations, and/or associated illness of the patient), locations of medical procedures, doctors involved in the medical procedures, and the like.

In the embodiment illustrated in FIG. 6, the database 628 includes an external bone database 630 ("bone database 630") and an external pathology analysis database 632 ("pathology analysis database 632"). The bone database 630 can store bone condition data (e.g., diagnoses of normal, cancerous, osteoporosis, and the like) for a plurality of patients, and/or information related to the test(s) performed on each patient (e.g., values from a scan using the hybrid MWPM component 610, DEXA results, X-ray results, and the like). For example, for patient 1, the information in the bone database 630 can include the BMD value from at least one test performed on a bone sample from patient 1 (e.g., a BMD value of 4), the MWPM value provided by the hybrid MWPM component 610 (e.g., an MWPM value of 700 nm), a threshold MWPM value for the patient (e.g., of 750 nm), and/or a diagnosis of the bone sample from patient 1 (e.g., given the BMD, MWPM, and threshold values above, that patient 1 has a normal bone). In some embodiments, the pathology analysis database 632 stores data similar to the bone database 630 and/or data related to various pathologies, conditions, and/or diseases that are not necessarily related to patients' bones. Purely by way of example, the data in the pathology analysis database 632 can indicate that patient 1 has inflamed tissue surrounding a specific bone sample that underwent a previous medical operation (e.g., a surgery to remove a bacterial infection from the bone). In another example, the data in the pathology analysis database 632 can include indications of various other pathological conditions the patient has (e.g., cancer, diabetes, lupus and rheumatoid arthritis, hyperthyroidism, celiac disease, asthma, multiple sclerosis, and/or any other pathological condition).

Figure 7:
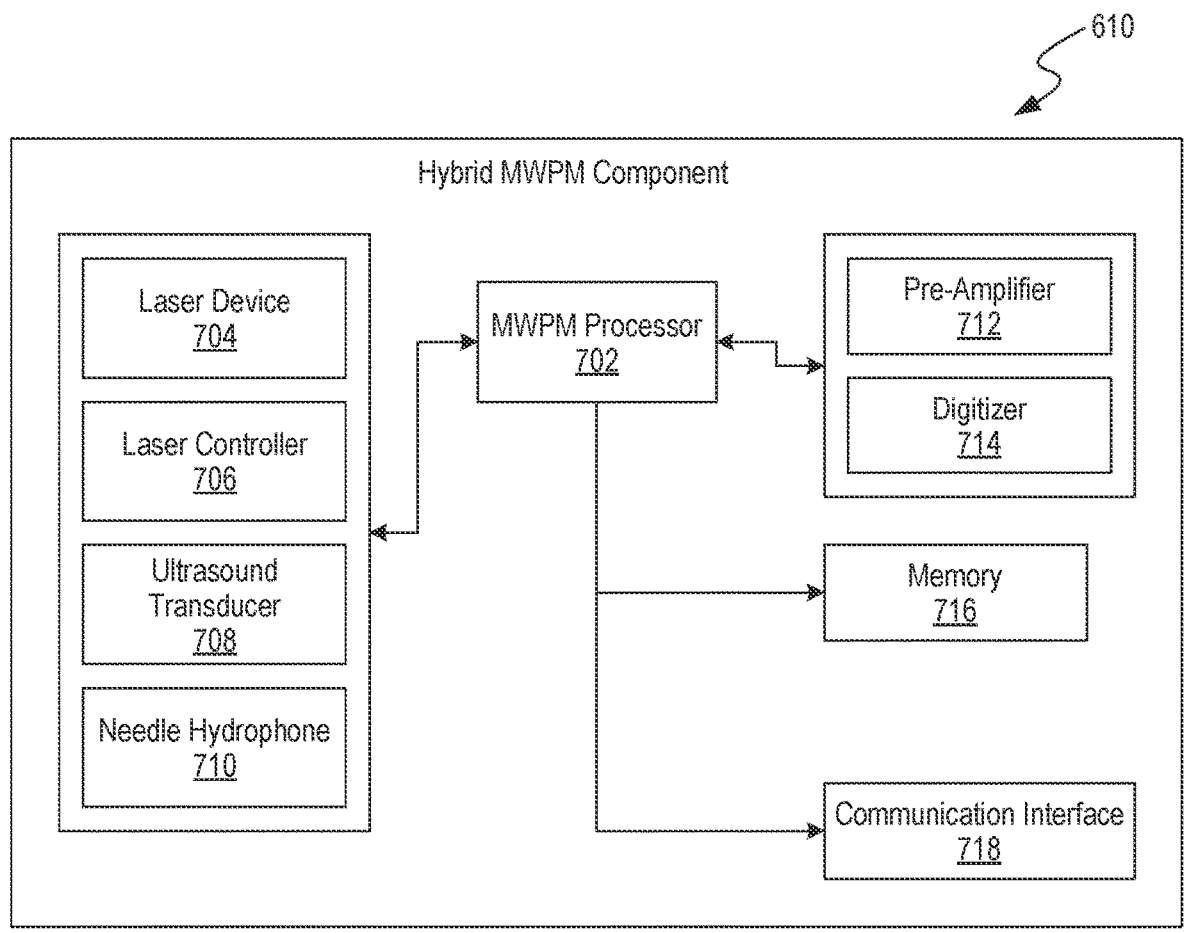
FIG. 7 is a block diagram of the hybrid MWPM component communicatively coupled in the system of FIG. 6 in accordance with some embodiments of the present technology.

FIG. 7 is a block diagram of the hybrid MWPM component 610 communicatively coupled in the system 600 of FIG. 6 in accordance with some embodiments of the present technology. In the illustrated embodiment, the hybrid MWPM component 610 includes an MWPM-specific processor 702 ("MWPM processor 702") that is operatively coupled to a laser device 704, a laser controller 706, an ultrasound transducer 708, a needle hydrophone 710, a pre-amplifier 712, a digitizer 714, a memory 716, and a communication interface 718. The hybrid MWPM component 610 can employ a variety of these components to perform one or more scans (e.g., tests) of the tissue sample (e.g., measurements of bone density, bone matrix composition, and the like) and/or to help analyze results from the test(s). In some embodiments, the scans are conducted in real-time using the hybrid MWPM component 610. In some embodiments, each of the components of the hybrid MWPM component 610 is operatively coupled to the power supply 608.

The MWPM processor 702 can facilitate programming of the plurality of components to perform their desired functions. For example, the MWPM processor 702 can be configured to control operation of the laser device 704 via the laser controller 706 (e.g., by activating and/or modulating the intensity of the laser device 704) and record measurements resulting from the laser's interactions with the tissue sample. The MWPM processor 702 can then retrieve information from the laser device 704, the ultrasound transducer 708, and/or the needle hydrophone 710 (e.g., intensity of the laser device 704, during operation, values related to photoacoustic signals from the tissue sample, and the like) and direct the information to the operating room 602.

The laser device 704 can be configured to impart a light beam with a predetermined (or calibrated) laser intensity over a sample once the hybrid MWPM component 610 is turned on. In some embodiments, the laser device 704 is a neodymium-doped yttrium aluminum garnet (Nd:YAG) laser. In some embodiments, the light beam generated by the laser device 704 is divided into two or more parts to help increase the accuracy of any measurement performed by the laser device 704. For example, a first part of the light beam (sometimes also referred to herein as a "reference beam") can be projected onto a black rubber (or other suitable material) and then recorded by the ultrasound transducer 708 for calibration of subsequent signal magnitude. A second part of the light beam (sometimes also referred to herein as an "analysis beam") can be projected onto the tissue sample. The reference beam can be used to calibrate the magnitude of the light beam, while the analysis beam is imparted over the tissue sample to excite a photoacoustic signal from the tissue and/or to generate optical measurements near the surface of the tissue.

In some embodiments, the laser controller 706 is configured to modulate the laser intensity (e.g., magnitude) of the laser device 704 and/or the wavelength of the light beam. In some embodiments, the laser controller 706 is configured to control the orientation, position, and/or movement of the laser device 704 during operation (e.g., to move the laser device 704 during a scan). In some embodiments, the laser device 704 measures a $\mu_a$ value of the tissue sample to detect cracks or indentations over the sample in addition to, or in alternative to, various photoacoustic measurements.

In some embodiments, the hybrid MWPM component 610 employs the ultrasound transducer 708 to measure and/or detect a material density of the tissue sample (e.g., to detect a bone material density (BMD)). The ultrasound transducer 708 is a sound-related sensor that sends electrical signals to the tissue sample (e.g., the bone) that strike the tissue sample and revert back to the ultrasound transducer 708 and/or another measuring device, such as the needle hydrophone 710. The ultrasound transducer 708 can further excite the photoacoustic signal, which is then measured by the needle hydrophone 710. Additionally, or alternatively, the ultrasound transducer 708 can be used to detect and/or identify irregularities in the tissue sample. For example, the ultrasound transducer 708 can receive a signal from the MWPM processor 702 to vibrate at a predefined frequency, thereby generating and directing sound waves into the tissue sample. The sound waves travel through the tissue sample (e.g., through the bone) and are redirected back to the ultrasound transducer 708 (and/or the needle hydrophone 710) when they are incident on an irregularity. In various embodiments, the irregularity can include, cracks, holes, and/or inconsistency in the BMD. In some embodiments, the sound waves generated are reflected back to the ultrasound transducer 708 in the form of an echo signal. In such embodiments, the ultrasound transducer 708 can convert the echo signal into an electrical signal for the MWPM processor 702. The ultrasound transducer 708 can calculate the time interval between sending the sound wave into the sample and receiving the echo signal, send the time interval to the MWPM processor 702, and the MWPM processor 702 can use the time interval to help evaluate the tissue sample.

In some embodiments, the needle hydrophone 710 includes a piezo-ceramic hydrophone sensor that can provide ultrasonic field mapping with pinpoint access and high spatial resolution. In some embodiments, the hybrid MWPM component 610 includes multiple of the needle hydrophones 710, each directed towards the tissue sample and configured to generate an ultrasonic field map. In some embodiments, the needle hydrophone 710 performs functions related to analysis of the sample with decreased sensitivity flatness and narrower directivity. In some embodiments, the photoacoustic signal received by the needle hydrophone 710 is fed to the pre-amplifier 712 to amplify its magnitude. In some embodiments, the photoacoustic signal is routed to the pre-amplifier 712 as an electric signal via the MWPM processor 702. In other embodiments, the needle hydrophone 710 routes the photoacoustic signal directly to the pre-amplifier 712.

The digitizer 714 can be configured to convert analog signals into digital signals before and/or after they are amplified. In some embodiments, the digitizer 714 converts the amplified photoacoustic signal into the real-time data to be stored in the database 616 and/or the memory 716. Further, the memory 716 can store parameters related to the test(s) of the tissue sample (e.g., operating parameters such as the wavelength of the lase, magnitude of the laser, frequency of the ultrasound sound waves; the density, porosity, and/or matrix structure of the tissue sample; MWPM values; $\mu_3$ values; and the like). In some embodiments, the converted signals from the digitizer 714 are stored in the memory 716, and then sent to the database 616 via the communication interface 718 for further analysis or use. In a specific, non-limiting example, the memory 716 can store data that the laser device 704 generates a light beam with an energy-per-laser-pulse in a range between 15 millijoules per square centimeter ($mJ/cm^2$) to 20 $mJ/cm^2$ with a diameter of about 4 millimeters (mm), and the beam splitter divides the light beam into two components in 1:9 ratios (reference beam:analysis beam). Additionally, or alternatively, the memory 716 can store values generated using the light beam above, such as BMD value of 2.5, an MWPM value of 750 nanometers (nm), and a $\mu_a$ value of 2.

The communication interface 718 can connect the hybrid MWPM component 610 to external resources (e.g., via the internet), such as shared pools of configurable resources and higher-level services that can be rapidly provisioned with minimal management effort. Additionally, or alternatively, the communication interface 718 can be communicatively coupled to the operating room 602 via the communication interface 620 (FIG. 6) to be communicatively coupled to the user interface 606, the memory unit 614, the base module 618, and/or the processor 604 for real-time assistance in the operating room 602. Additionally, or alternatively, the communication interface 718 can be synchronized with the database 616 (FIG. 6) to store information associated with operating room 602. In some embodiments, the communication interface 718 is referred to as an internal communication component that facilitates internal communications of the operating room 602, while the cloud network 624 (FIG. 6) is referred to as an external communication component that facilitates communication between the external equipment 622 and the operating room 602.

Referring back to FIG. 6, the base module 618 of the operating room 602 can be configured to retrieve information related to the analysis of the tissue sample from the database 616, the bone database 630, and/or the databases 628. Further, the base module 618 can be configured to control, direct, and/or perform operation of the operating room 602 in real-time.

Figure 8A:
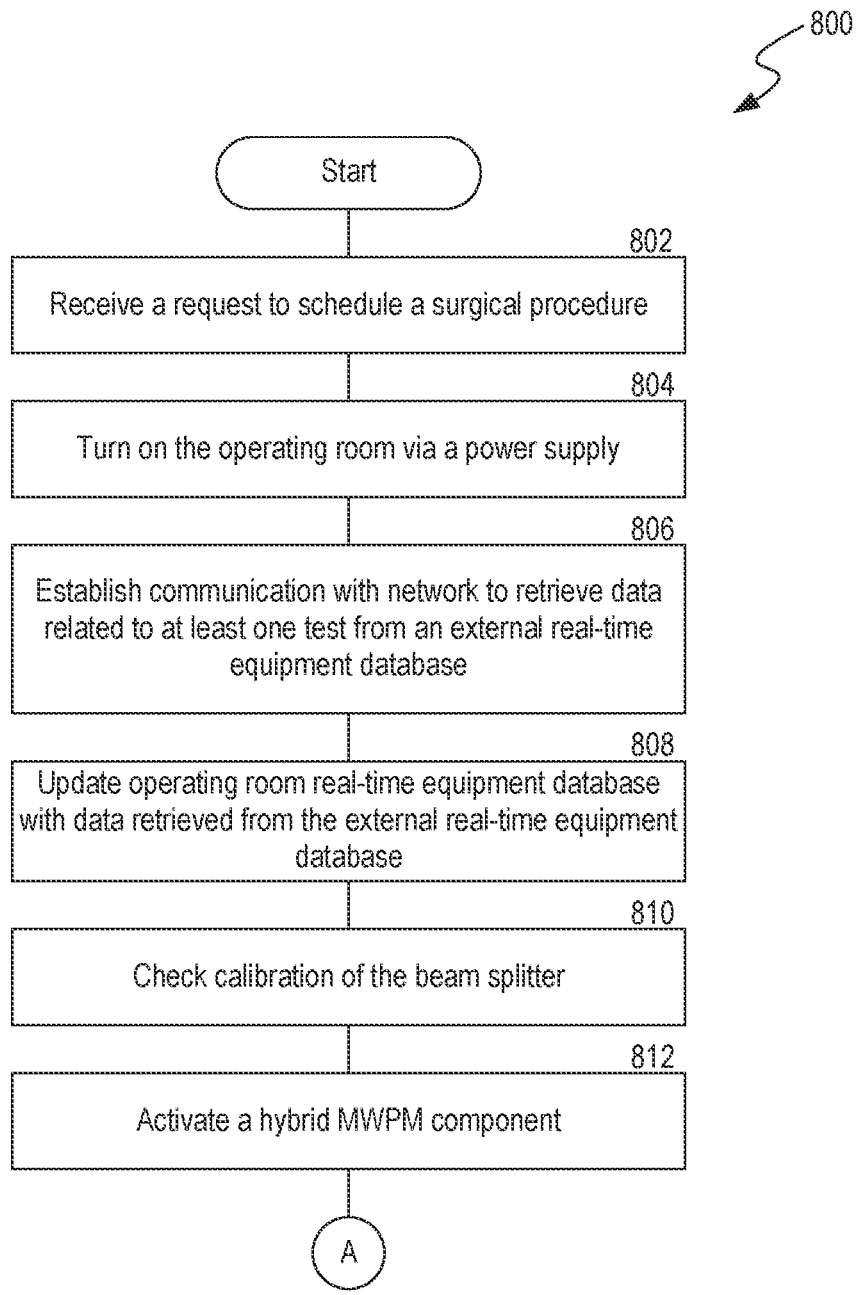
FIGS. 8A and 8B are flow diagrams of a process for operating an operating room in accordance with some embodiments of the present technology.
Figure 8B:
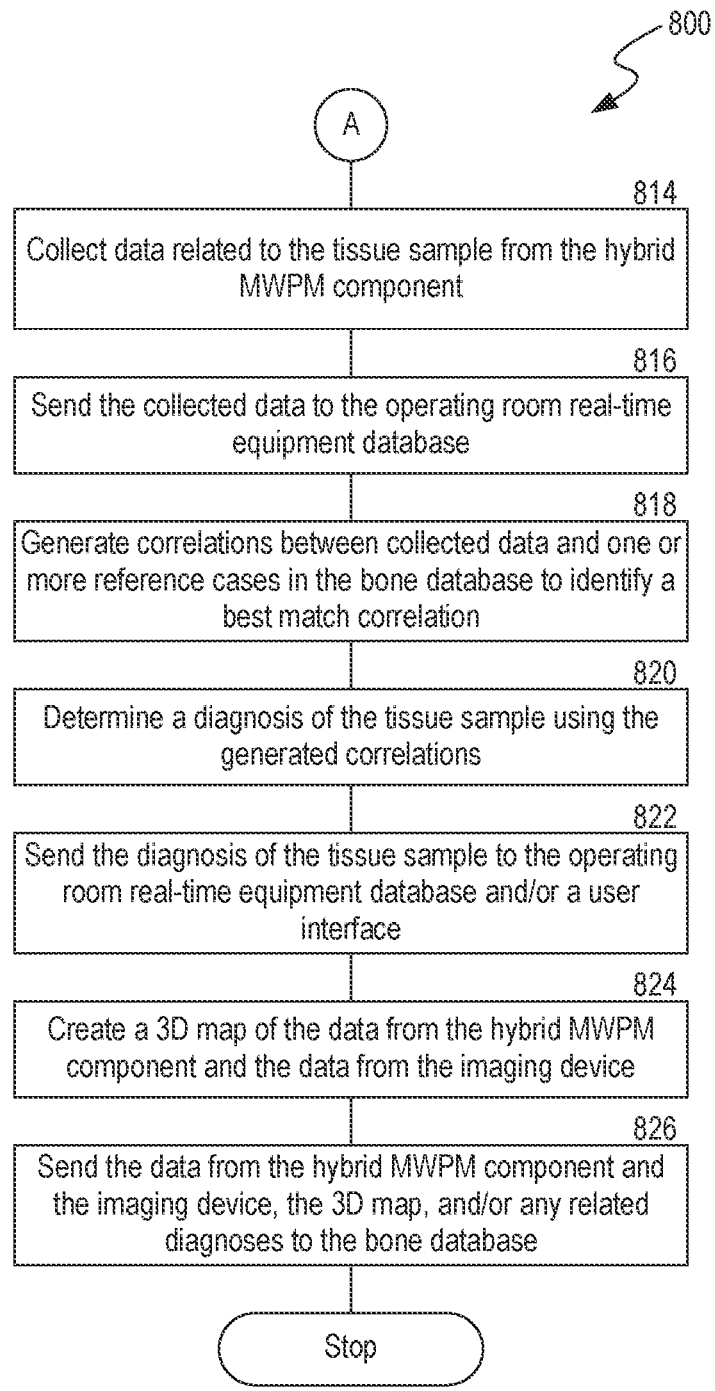

FIGS. 8A and 8B are flow diagrams of a process 800 for operating the operating room 602 of FIG. 6 in accordance with some embodiments of the present technology. The process 800 can be executed by the base module 618, or other suitable component (e.g., the base module 626), to execute at least a part of a medical procedure to analyze and/or diagnose a tissue sample (e.g., a user's bone). Below, FIGS. 8A and 8B are explained in conjunction with references to FIGS. 6, 7, and 9-12. It will be understood that, in some embodiments, one or more of the functions noted in the blocks may occur out of the order noted in the drawings. For example, two blocks shown in succession in FIGS. 8A and 8B can be executed concurrently, or substantially concurrently. In another example, blocks can sometimes be executed in an alternative order, depending upon the functionality involved. In yet another example, the blocks of the process 800 can be split for execution between two or more components. In still further examples, one or more of the blocks discussed below can be omitted from the process 800 altogether. In addition, the process descriptions or blocks in flow charts should be understood as representing decisions made by a hardware structure such as a state machine.

The process 800 begins at block 802 with receiving a request from a surgical site to schedule the surgical procedure for performing real-time analysis of the tissue sample. In various embodiments, the process 800 can receive the request from the surgical site (e.g., at the operating room 602) and/or a remote location. In some embodiments, the request can include directions for scheduling a surgical procedure for performing real-time analysis of a tissue sample. The directions can include the allocation of equipment (e.g., any of the components of the operating room 602, ventilators, operation-specific equipment, and/or other equipment required at the surgical site) and personnel for the surgical procedure. Purely by way of example, the request can include an indication that a patient (e.g., "Alex") is being admitted at a surgical facility in New York, USA; that the operating room 602 needs to perform surgery with real-time analysis of bone tissue to help analyze and diagnose Alex's bones, and that the surgical procedure will be conducted under the supervision of Dr. Van. In some embodiments of this example, the base module 618 receives the request from the surgical facility in New York to schedule the surgery for Alex.

At block 804, the process includes activating power for the operating room 602 via the power supply 608 in conjunction with the initiation module. In some embodiments, the initiation module performs functions related to communication between the operating room 602 and the external equipment 622. In some embodiments, the base module 618 communicates with the processor 604 of the operating room 602 to turn on the power supply 608. Further, at block 806, the process 800 includes establishing communication with the external equipment 622 to retrieve data related to previous tests for the patient (e.g., relevant values from Alex's previous surgical procedures), reference cases, and/or predetermined medical threshold values for one or more diagnosis. Purely by way of example, the base module 618 can retrieve, from the bone database 630, one or more predetermined threshold values associated with osteoporosis (e.g., that osteoporosis is considered for MWPM measurements with a value range between about 700 nm and about 950 nm, a threshold value of 750 nm or greater, and a BMD value of less than −2). In some embodiments, the process 800 executes block 806 using the initiation module within the base module 618. In various embodiments, the initiation module can retrieve the data over the cloud network 624 and/or any other suitable network connection.

At block 808, the process 800 includes updating the database 616 with the data retrieved from the database 628. Purely by way of example, as illustrated in FIG. 9, the database 616 can be updated with values associated with one or more (four shown) measurements during a previous surgical procedure. In the illustrated embodiment, for example, the database 616 has been updated with values from 1:25:30 PM that include BMD value of 2.5, an MWPM of 750 nm, and a $\mu_a$ value of 2; values from 1:25:35 PM that include a BMD value of 0.9 with an MWPM of 780 nm, and a $\mu_a$ value of 2.5; values from 1:25:40 PM that include a BMD value of 2.0 with an MWPM of 705 nm, and a $\mu_a$ value of 3; and values from 1:25:45 PM that include a BMD value of 1.5 with an MWPM of 710 nm, and a $\mu_a$ value of 2. Each of the updates can also be associated with an observation and/or diagnosis based on the measured values. For example, at 1:25:30 PM the values indicated high-density bone material, while at 1:25:35 PM the values indicated porous bone material. Returning to the description of FIGS. 8A and 8B, in some embodiments, block 808 can be executed at least partially by the initiation module.

At block 810 the process 800 includes checking the calibration of the beam splitter. In one embodiment, the base module 618 may split the light beam generated by the laser device 704 into the reference beam and the analysis beam using the beam splitter. For example, the base module 618 can check that the beam splitter divides the light beam from the laser device 704 (FIG. 7) in a 1:9 ratio (or other suitable ratio), that the diameter of the light beam is about 4 mm, and/or that the light beam has an energy-per-laser-pulse between about 15 mJ/cm² and about 20 mJ/cm². In some embodiments, block 810 can be executed at least partially by the initiation module.

At block 812, the process 800 includes activating the hybrid MWPM component 610 (FIG. 6), for example via the polling module of the base module 618. In some embodiments, the activation of the hybrid MWPM component 610 to initiate testing of the sample by imparting the analysis beam to illuminate the sample from one side at specific operating parameters. Purely by way of example, the base module 618 can activate the hybrid MWPM component 610 by setting the energy-per-laser-pulse in the light beam from the laser device 704 at 15 mJ/cm² with a broad bandwidth at 450 MHz, and instructing the hybrid MWPM component 610 to begin emitting pulses. In some embodiments, block 812 can be executed at least partially by the polling module.

In various embodiments, each sub-modules of the base module 618 (e.g., the initiation module, the polling module, and the like) can execute their functions above in blocks 804-812 concurrently and/or in a succession alternative to the order discussed above. In some embodiments, the order of the execution of blocks 804-812 is at least partially dependent upon the input request received at the base module 618 at block 802.

At block 814, the process 800 includes collecting data related to the tissue sample, from the hybrid MWPM component 610 and/or an imaging device. In some embodiments, the process 800 collects the data periodically in a predefined time frame. In various embodiments, the predefined time frame can be set by the processor 604 of the operating room 602 (FIG. 6) according to the pulse width of the light beam emitted by the laser device 704, according to a movement speed of the laser device 704 (e.g., a scan speed), a requested sample period, and/or any other suitable constraint. In a specific, non-limiting example, the base module 618 can collect data every 1, 2, 5, 10, 50, and/or 100 milliseconds (ms), and/or after any other suitable period. Returning to the example of FIG. 9, the predefined time frame in the retrieved data was every five seconds. In some embodiments, block 814 can be executed at least partially by the polling module.

At block 816, the process 800 includes sending the collected data to the database 616, along with any suitable related information. For example, the base module 618 can send data indicating that an MWPM value of 800 nm was received from the tissue sample by illuminating one side of the target bone tissue with the energy-per-laser-pulse of 15 mJ/cm² from the laser device 704. In some embodiments, block 816 can be executed at least partially by the polling module.

Successively, at block 818, the process 800 includes generating one or more correlations of real-time data from the surgical procedure (e.g., Alex's tissue sample data) to one or more reference cases in the bone database 630 e.g., tissue sample data for patients 1-N) to identify one or more best match correlations. As discussed above, data from the best match correlation(s) can be used to help analyze the real-time data and/or to help diagnose the tissue sample. In some embodiments, the base module 618, using an AI/ML algorithm, generates the correlations between the data received from the hybrid MWPM component 610 and the data retrieved from the bone database 630 in real-time to identify one or more closely related correlations in the reference cases. Purely by way of a simplified example, the base module 618 can correlate the real-time data acquired from the hybrid MWPM component 610 (e.g., an MWPM value of 700 nm, a $\mu_a$ value of 2, and a BMD value of 2.5) with the retrieved data from the bone database 630. In this example, the base module 618 can identify reference cases with similar values from the scan, as well as threshold values based on the similar cases (e.g., a threshold limit of 750 nm for osteoporosis based on the reference cases that are diagnosed with osteoporosis typically having an MWPM value below 750 nm). Accordingly, in this example, the base module 618 can identify that the MWPM value of 700 nm is below the threshold limit of 750 nm for osteoporosis consideration and diagnose osteoporosis in the target bone tissue (e.g., despite the BMD value of 2.5). In some embodiments, block 818 can be executed at least partially by the analysis module. The threshold limit for a condition can be selected or determined based on patient information (e.g., age of the patient, gender, race, etc.). For example, threshold limits for osteoporosis consideration and diagnosis can decrease with the patient's age to account for normal age-related bone-density decrease. Additionally, or alternatively, the threshold limits can be determined using machine-learning techniques disclosed herein.

The values from the scan can be used to provide a confidence score of the diagnosis, diagnose other conditions, etc. In some embodiments, the base module 618 generates an aggregate score based on selected weighted values from the scan, then uses the aggregate score to characterize the tissue sample, diagnose conditions, or the like. The similar values in the reference cases can be identified within ranges of values (e.g., absolute ranges, percentage ranges, etc.), threshold values, and/or determined values using, for example, ML training sets, user input, etc. The system can be programmed with one or more correlation rules for conditions, patient groups, etc. In supervised training, a user can select training sets of reference data in which pathology and accuracy of detected values have been validated. In unsupervised training, the system can select validated reference data sets and can be retrained any number of times.

At block 820, the process 800 includes determining a diagnosis of the tissue sample using the generated correlation(s), the identified reference cases, and/or any other suitable data from the bone database 630 (e.g., diagnoses in the reference cases). In some embodiments, the base module 618 determines the diagnosis based at least partially based on diagnoses in the identified reference cases. For example, the base module 618 can mine data from the reference cases to determine that an MWPM value of 700 nm received from the tissue sample, with a BMD value of 2.5, and a $\mu_a$ value of 2, exceeds a BMD threshold value of −2 identified in the reference cases as a threshold for osteoporosis. As a result, the base module 618 can diagnose that the bone tissue does not fall within the osteoporosis group. In some embodiments, block 820 can be executed at least partially by the analysis module.

At block 822, the process 800 can include sending the diagnosis to the database 616 and/or the user interface 606. For example, the base module 618 can send an indication to the database 616 that the tissue sample does not fall within the osteoporosis group, along with an indication of the rationale (e.g., because the results indicated that the tissue sample had a BMD value above the threshold value) secondary support (e.g., that the tissue sample had an MWPM value below the threshold limit, imagery of the tissue sample corroborated the diagnosis, and the like), and/or a record of the values from the scan and related information (e.g., operating parameters during the scan).

At block 824, the process 800 includes generating a 3D map of the data from the hybrid MWPM component 610 (e.g., the values from the scan, diagnostic information, and the like), and/or any linked data from the imaging device (example shown in FIG. 10, discussed in more detail below). For example, the data from the imaging device can be mapped with the hybrid MWPM component 610 using time stamps and/or metadata indicating the relative position and/or orientation of the imaging device and the hybrid MWPM component 610. In some embodiments, the imaging device and the hybrid MWPM component 610 are contained within the same end effector (e.g., when the imaging device 611 is used), and are therefore automatically linked. In some embodiments, the imaging device and the hybrid MWPM component 610 are positioned on exact opposite sides of the tissue sample (e.g., when a secondary imaging device is used), and are linked through a well-posed inversion. In various other embodiments, the process 800 uses the data on the orientation, position, and/or movement of each of the components of the hybrid MWPM component 610 during the scan to construct a 3D map with similar data on the orientation, position, and/or movement of the imaging device during the scan.

Figure 10:
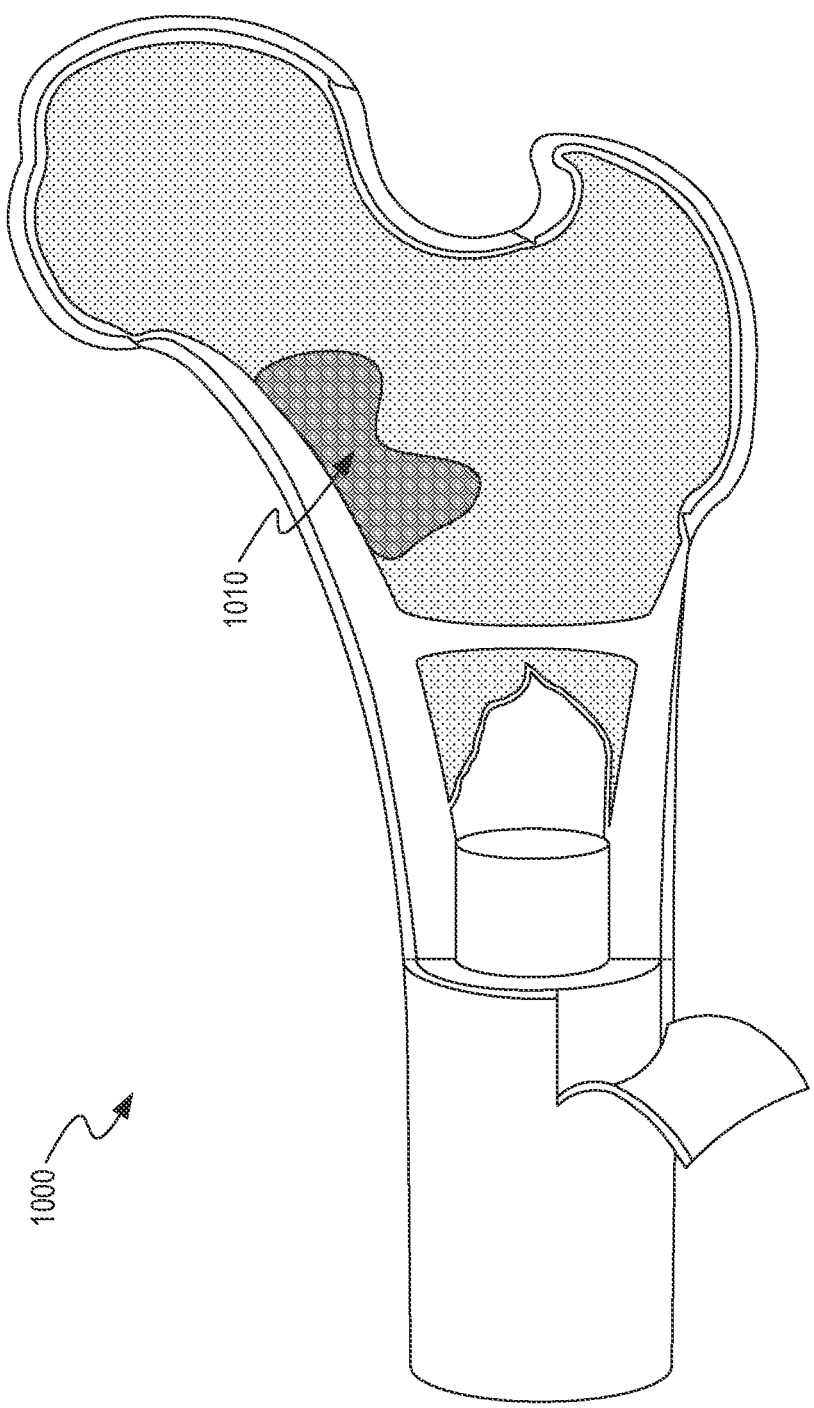
FIG. 10 illustrates an example of a three-dimensional map that can be generated during real-time analysis of bone tissue in accordance with some embodiments of the present technology.

FIG. 10 illustrates an example of a 3D map 1000 in accordance with some embodiments of the present technology. The 3D map 1000 can allow the doctor to view the real-time data in three dimensions to analyze the tissue sample concurrently with the process 800 and/or to review diagnoses determined at block 820. In some embodiments, the process 800 maps the diagnoses with the data of the imaging device to create the 3D map 1000 of the results for the doctor to analyze. In some embodiments, the 3D map 1000 highlights regions of the tissue sample according to the diagnoses and/or the values from the hybrid MWMP component 610. For example, the 3D map 1000 can highlight (or otherwise emphasize) regions with BMD values that are within a particular range and/or MWPM values within another particular range. In the illustrated embodiment, for example, the 3D map 1000 emphasizes region 1020 via a change in shading from the surrounding regions. The emphasis can help direct the doctor's review of the 3D map 1000 and/or further analysis of the patient. In some embodiments, the process 800 creates the 3D map 1000 including raw data from at least one of the BMD values and the MWPM values, allowing the doctor to perform an independent diagnosis of the tissue sample. In various embodiments, the raw data can be indicated via differences in shading, color, fill patterns, express indications, display tables, selectable displays, and/or in any other suitable manner. In some embodiments, the 3D map 1000 includes selectable layers. For example, the 3D map 1000 can include a first layer created with the BMD values, a second layer created with the MWPM values, and a third layer with data correlated from an imaging device. As further illustrated in FIG. 10, the selectable layers in the 3D map 1000 can be related to one or more regions and/or depths within the bone. In some embodiments, block 824 can be executed at least partially by the mapping module.

In some embodiments, the values from the scan, along with any identified reference cases, are sent to the auxiliary user interface for a doctor, surgeon, or other medical professional to perform real-time analysis of the data. In some such embodiments, the auxiliary interface also displays data from the imaging device (e.g., in the form of a picture, image, and/or video). Accordingly, in such embodiments, the doctor, surgeon, or other medical professional can conclude a final diagnosis based on the values from the scan, the reference cases, diagnoses from block 820, and/or the data captured by the imaging device. Purely by way of example, the process 800 can create the 3D map, with selectable layers showing that the BMD value ranges from 1.5 to 4 through the tissue sample, with an average (or mean) value above the threshold value of 2; the MWPM value ranges from 500 nm to 900 nm, with an average (or mean) value below the threshold limit of 750 nm for the osteoporosis group; the data from the imaging device indicating high density in the structure of the bone (e.g., supporting the average BMD value above the threshold value); and the diagnosis from block 820 of a normal bone. In this example, the doctor, surgeon, or other medical professional may conclude that the bone tissue does not have osteoporosis, but may want to further review regions with an MWPM value below 750 nm. For example, the mapped data may indicate a range of values suggesting that minor osteoporosis and/or a transition state from a healthy bone in a few regions that can be identified by the doctor while reviewing all of the data together. Accordingly, the generated 3D map can help increase early identification of bone regions with pathological conditions (e.g., before the conditions become widespread).

At block 826, the process 800 includes sending the data from the scan, the diagnosis from block 820, the 3D map, and/or the diagnosis from the doctor (or other medical professional) to the bone database 630. For example, the base module 618 can send information indicating the BMD value is 2.5, the threshold value for BMD was set at 2, the MWPM value is 700 nm, the threshold value for MWPM was set at 750 nm, the captured image supporting the real-time data, and/or a confirmation of the doctor's diagnosis of the bone. In one embodiment, the base module 618 updates the bone database 630 over the cloud network 624. In some embodiments, block 826 can be executed at least partially by the communication module.

The base module 626 of the external equipment 622 can be configured to retrieve, from the database 616, information related to the analysis of the tissue sample. Further, as noted above, the base module 626 can be configured to perform the operation of the operating room 602 in real-time in accordance with the process 800 discussed above.

Figure 11:
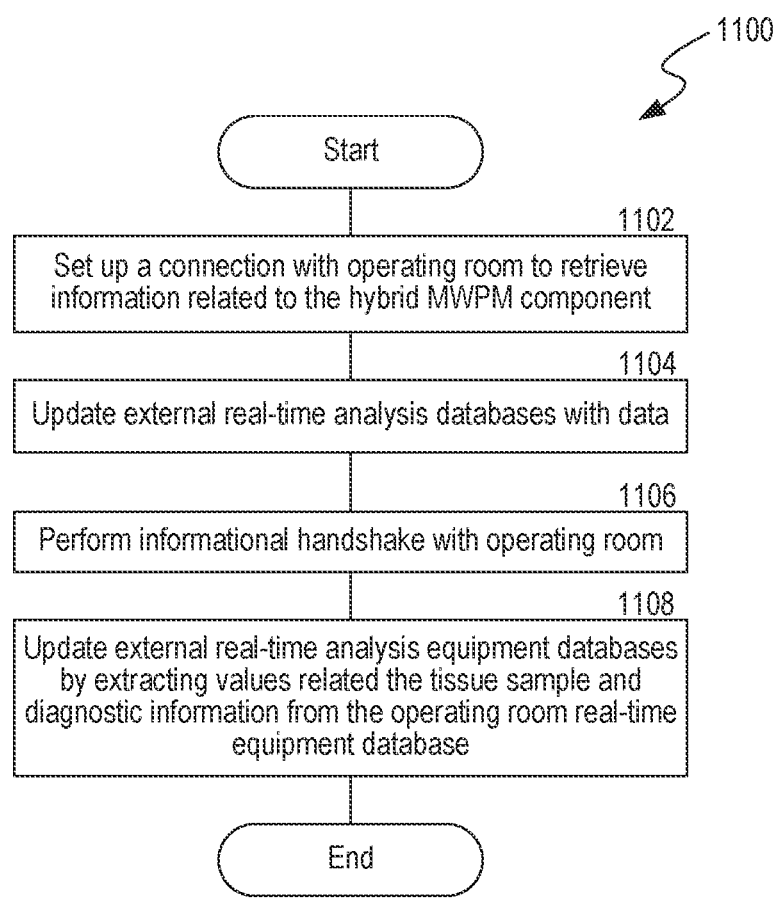
FIG. 11 is a flow diagram of a process transferring information to an external equipment in accordance with some embodiments of the present technology.

Additionally, or alternatively, the base module 626 can be configured to control the external equipment 622 in real-time in conjunction with the processes in the operating room 602. FIG. 11 is a flow diagram of a process 1100 transferring information to the external equipment 622 in accordance with some embodiments of the present technology. The process 1100 is described in conjunction with the bone database 630 illustrated in FIG. 12 and the pathology analysis database 632 illustrated in FIG. 13. FIG. 11 is also explained in conjunction with various details from FIGS. 6-9. It will be understood that, in some embodiments, one or more of the functions noted in the blocks may occur out of the order noted in the drawings. For example, two blocks shown in succession in FIG. 11 can be executed concurrently, or substantially concurrently. In another example, blocks can sometimes be executed in an alternative order, depending upon the functionality involved. In yet another example, the blocks of the process 1100 can be split for execution between two or more components. In still further examples, one or more of the blocks discussed below can be omitted from the process 1100 altogether. In addition, the process descriptions or blocks in flow charts should be understood as representing decisions made by a hardware structure such as a state machine The process 1100 begins at block 1102 by establishing a connection with the operating room 602 to retrieve information related to the hybrid MWPM component 610. In some embodiments, the base module 626 facilitates connection to the operating room 602 (e.g., via the cloud network 624 and/or another suitable network), to retrieve data related to the hybrid MWPM component 610 from the database 616. In one example, the retrieved information can include operating parameters the hybrid MWPM component 610 and/or recent calibration data related to the hybrid MWPM component 610. In another example, the base module 626 can retrieve data that a specific patient (e.g., Alex) is being evaluated for bone-related conditions and is going to be tested for osteoporosis (or related pathologies) using the hybrid MWPM component 610. In this example, the base module 626 can retrieve the predetermined thresholds (e.g., the BMD threshold value is 2 and/or the MWPM threshold value is 950 nm) and/or the real-time data for Alex's bone tissue (e.g., Alex's BMD value is 2.5 and/or Alex's MWPM value is 900 nm, each indicating no osteoporosis). Additionally, or alternatively, the base module 626 can retrieve calibration data related to hybrid MWPM component 610. Purely by way of example, the calibration data can include post-measurement adjustments, such as lowering the MWPM value by 2 nm for correction.

At block 1104, the process 1100 includes updating the database 628. In some embodiments, the process 1100 allows researchers to update the bone database 630 (example shown in FIG. 12, discussed in more detail below) and/or the pathology analysis database 632 (example shown in FIG. 13, discussed in more detail below) according to the diagnosis and/or values from the tissue sample (e.g., Alex's raw values and Alex's bone diagnosis). Additionally, or alternatively, researchers (or other appropriate external groups such as a board of medical professionals) can update the bone database 630 and/or the pathology analysis database 632 with data from tests conducted over a plurality of tissue samples and/or patients, along with the corresponding diagnoses from a doctor or other medical professional. In some embodiments, the plurality of tests are experimental and/or conducted to gather data, rather than for clinical purposes. In a specific example, the plurality of tests can provide reference cases with a variety of operating parameters for the hybrid MWPM component 610. In another example, the process 1100 allows the researchers to update the bone database 630 with an analysis of numerous samples conducted using the hybrid MWPM component 610 at specific operational settings. In some embodiments, the data results from a clinical trial. Additionally, or alternatively, the data can be included to increase the diversity of observational and/or training data for the AI/ML. In each case, the updates to the bone database 630 and/or the pathology analysis database 632 increase the body of potential reference cases that can be identified at block 818 of FIG. 8B. In some embodiments, block 1104 is executed by a research module in the base module 626.

FIG. 12 illustrates the bone database 630 in accordance with some embodiments of the present technology. As illustrated in FIG. 12, the bone database 630 is configured to store data related to the analysis of the tissue sample for multiple patients, such as the diagnosis for each patient and/or the data related to that diagnosis. In some embodiments, the bone database 630 includes one or more subsets of grouped and/or paired data sets of data (e.g., all patients with a given BMD value, all patients with a given diagnosis, and the like). Further, the bone database 630 can store specific data points (e.g., the MWPM value along with descriptions from the imaging device) for each patient, along with a diagnosis of the tissue sample, such as osteoporosis and/or normal bone. In the illustrated example, the bone database 630 stores that for a first region of patient 1, the imaging device recorded high density structures; the hybrid MWPM component 610 measured an MWPM value of 730 nm and a BMD value of 2.2; and that the tissue sample was diagnosed as normal bone. In another example, the bone database 630 stores that for a second region of patient 1, the imaging device recorded porous structures; the hybrid MWPM component 610 measured an MWPM value of 780 nm and a BMD value of 1.8; and that the tissue sample was diagnosed as having osteoporosis.

FIG. 13 illustrates the pathology analysis database 632 in accordance with some embodiments of the present technology. In the illustrated embodiment, the pathology analysis database 632 is configured to store data related to the analysis of the tissue sample, bone tissue condition, inflamed tissue surrounding the target tissue, cancerous cells, and the like. Further, as illustrated in FIG. 13, the pathology analysis database 632 can store data associated with a plurality of patients, each of whom underwent some form of testing on their bodily tissue for pathological conditions and/or diseases. In some embodiments, the pathology analysis database 632 stores data related to the sample using the pathology component 612 and the measurements detected and/or monitored over the imaging device. The data can be related to diagnosed conditions of the monitored tissue samples, such as the patient having skin cancer. In some embodiments, the data is related to the analysis of the tissue sample includes a range of measurements and threshold values that the pathology component 612 received while measuring a tissue sample. In some embodiments, the threshold values indicate a maximum and a minimum value of data collected by the pathology component 612 while performing the analysis. In the illustrated example, the pathology analysis database 632 stores that for a patient 2, the pathology component 612 detected symptoms of skin cancer and the imaging device recorded melanoma and brown spots on patient 2's skin.

Returning to FIG. 11, at block 1106 the process 1100 includes performing an informational handshake with the operating room 602 to receive a transfer of data from the operating room 602. In some embodiments, the process 1100 performs the handshake continuously with the operating room 602 to receive constant updates to the bone database 630 and the pathology analysis database 632. In some embodiments, the process 1100 performs the handshake with the operating room 602 only once (e.g., concurrently with block 826 of FIG. 8B). In some embodiments, block 1106 is executed by an initiation module in the base module 626.

At block 1108, the process 1100 updates the database 628 by extracting the values from the hybrid MWPM component 610 and/or diagnostic data from the database 616. For example, the base module 626 can update the bone database 630 with the values from the scan (e.g., the raw data from the hybrid MWPM component 610) and/or the analysis performed on the tissue sample using raw data. In a specific example, the update to the bone database can include recording measurements of the patient's BMD value of 2.5, the MWPM value of 900 nm, and a related diagnosis is that the bone tissue does not have osteoporosis.

In some alternate embodiments, the surgical procedure, and any updates to relevant databases, is fully autonomous and executed by the operating room 602. The automation can allow for measurements and analysis without the input and/or intervention of a doctor. As a result, the automation can increase access to the processes disclosed herein, thereby helping to detect bone conditions early. In some embodiments, the surgical procedures described herein are fully controlled manually by the doctor in conjunction with the hybrid MWPM component 610 and/or the pathology component 612. In such embodiments, the doctor's use of the hybrid MWPM component 610 can help increase the accuracy of their diagnosis and/or allow them to provide a real-time diagnosis (e.g., instead of waiting for biopsy results). In some embodiments, the surgical procedures described herein are executed via a hybrid process, where a few parts are manually controlled and other parts are completed autonomously or semi-autonomously (e.g., with the doctor acting as a check to the hybrid MWPM component 610). In some such embodiments, a surgical robot utilizing the data from the bone database 630 can propose an action for review by the doctor, surgeon, or other medical professional. If the action is approved, the hybrid MWPM component 610 can execute the action. In some semi-autonomous embodiments, the hybrid MWPM component 610 performs the functions of analyzing bone tissue using real-time data from the bone database 630 of the external equipment 622, then presents the diagnoses to the doctor, surgeon, or other medical professional for review.

It will be appreciated by those skilled in the art that changes could be made to the exemplary embodiments described above without departing from the broad inventive concept thereof. It is to be understood, therefore, that this disclosure is not limited to the particular embodiments disclosed, but it is intended to cover modifications within the spirit and scope of the subject disclosure as disclosed above.

EXAMPLES

The present technology is illustrated, for example, according to various aspects described below. Various examples of aspects of the present technology are described as numbered examples (1, 2, 3, etc.) for convenience. These are provided as examples and do not limit the present technology. It is noted that any of the dependent examples can be combined in any suitable manner, and placed into a respective independent example. The other examples can be presented in a similar manner.

In some examples systems, the system can (1) perform multiple measurements, (2) determining a set of measurements corresponding to targeted tissue, (3) determining correlations between measurements in the set and/or between the set of measurements and reference data set, and (4) generating one or more multi-modality outputs (e.g., composite image, score, report) for the targeted tissue based on the correlations. The system can perform scans for obtaining the measurements. The system can identify when the device is located at target position for analyzing the tissue.

1. A computer-implemented method for real-time mapping and analysis of bone tissue, the method comprising:
    receiving, from a bone tissue mapper device, patient data of a patient,
        wherein the bone tissue mapper device includes a hybrid multi-wavelength photoacoustic measurements (MWPM) unit, and
        wherein the received patient data includes one or more images of at least one target tissue of the bone tissue and at least one measurement of the at least one target tissue from the hybrid MWPM unit;
    correlating, using a computing system, the at least one measurement to a plurality of stored reference cases;
    identifying, using the computing system, one or more reference cases, from the plurality of stored reference cases, based on one or more correlations between the at least one measurement received from the hybrid MWPM component and previous measurements in each the plurality of stored reference cases;
    determining, using the computing system and based on the one or more identified reference cases, a diagnosis of a bone condition of the at least one target tissue;
    generating, using the computing system, a diagnostic map of the bone tissue based on the image data and the diagnosis of the bone condition of the at least one target tissue; and sending, using the computing system, the diagnostic map to a computing device accessible by a surgeon.

2. The method of example 1, wherein the diagnostic map includes a three-dimensional (3D) bone map of a bone in the at least one target tissue, and wherein the method further comprises:

analyzing the 3D bone map using a machine learning model trained using bone tissue training sets to determine at least one surgical step based on the 3D bone map; and performing, using a robotic surgery system, the at least one surgical step on the patient.

3. The method of any of examples 1 and 2 wherein the at least one measurement includes a measurement of one or more of: bone mineral density, an $\mu 3$ value, and a MWPM value.

4. The method of any of examples 1-3 wherein each of the plurality of reference cases includes measurements from a related hybrid MWPM component, one or more other measurements related to an associated patient, and diagnostic information for the associated patient.

5. The method of any of examples 1-4 wherein the correlations are identified using an artificial intelligence or machine learning (AI/ML) algorithm.

6. The method of any of examples 1-5 wherein the at least one measurement is at least one first measurement received at a first time, and wherein the method further comprises:

receiving at least one second measurement of the at least one region of the patient from the hybrid MWPM component at a second time, wherein identifying the one or more reference cases is further based on correlations between the at least one second measurement and previous measurements of the plurality of reference cases.

7. The method of any of examples 1-6 wherein the diagnosis of the bone condition includes one or more of: osteoporosis, clinical osteopenia, bone cancer, normal bone with low or high bone mineral density (BMD), and/or osteomyelitis.

8. The method of any of examples 1-7 wherein sending the diagnosis of the bone condition to a computing device includes sending an indication of the correlations between the at least one measurement and the previous measurements for review by the surgeon.

9. A system for performing real-time analysis of bone tissue during a surgical procedure, the system comprising:

one or more computer processors; and a non-transitory computer-readable storage medium storing computer instructions, which when executed by the one or more computer processors, cause the system to:

receive at least one first measurement from a hybrid multi-wavelength photoacoustic measurements (MWPM) component, the at least one first measurement indicative of a first bone material density in a tissue sample of a patient;

receive image data of the tissue sample from an imaging device, wherein the imaging device is spatially coupled to the MWPM component;

retrieve a plurality of reference cases, wherein each reference case is associated with an individual reference patient, and wherein each reference case includes at least one second measurement indicative of a second bone material density in a tissue sample of the individual reference patient;

identify one or more reference cases from the plurality of reference cases based on correlations between the at least one first measurement and the at least one second measurement in each reference case;

determine, based on the one or more identified reference cases, at least one diagnosis of a bone condition in the tissue sample of the patient;

generating a diagnostic map of the tissue sample based on the image data and the at least one diagnosis of the bone condition in the tissue sample of the patient; and display, on a user interface accessible by a surgeon before or during a surgical operation on the patient, the diagnostic map.

10. The system of example 9, further comprising a network interface, wherein the computer instructions further cause the system to retrieve the plurality of reference cases from a third party database via the network interface.

11. The system of any of examples 9 and 10 wherein the diagnostic map includes a three-dimensional (3D) map the tissue sample of the patient based at least in part on the at least one first measurement and the image data.

12. The system of example 11 wherein the at least one first measurement is two or more first measurements, wherein the 3D map includes two or more selectable layers, and wherein each of the selectable layers is associated with a corresponding one of the two or more measurements.

13. The system of any of examples 11 and 12 wherein the at least one diagnosis of the bone condition is at least two diagnoses of the bone condition, wherein the 3D map includes two or more selectable layers, and wherein each of the selectable layers is associated with an individual one of the at least two diagnoses.

14. The system of any of examples 11-13, further comprising the imaging device, wherein the 3D map is further based at least in part on image data from the imaging device.

15. The system of any of examples 9-14, wherein the computer instructions further cause the system to:

monitor, through the imaging device, one or more specific aspects of bone tissue in the tissue sample of the patient based on diagnostic information in the one or more identified reference cases.

16. The system of example 15 wherein the one or more specific aspects of bone tissue include at least one of porous structures and high density structures.

17. A computer-implemented method for performing real-time analysis of bone tissue during a surgical procedure, the computer-implemented method comprising:

receiving, from a hybrid multi-wavelength photoacoustic measurements (MWPM) component, at least one measurement associated with tissue sample of a bone mass in a patient;

receiving, from an imaging device, image data related to the tissue sample, wherein the imaging device is coupled to the hybrid MWPM component to image the tissue sample from a single position;

identifying one or more reference patients from a plurality of reference cases based on correlations between the at least one measurement and previous measurements associated with previous tissue samples of bone mass in each of the plurality of reference cases;

determining, based on the one or more identified reference cases, a diagnosis of at least one bone condition of the patient;

generating a diagnostic map of the tissue sample based on the image data and the diagnosis of the at least one bone condition of the patient; and sending the diagnosis to a computing device accessible by a medical professional.

18. The computer-implemented method of example 17 wherein the hybrid MWPM component includes a laser device configured to emit a light beam used in performing the at least one measurement, and wherein the method further comprises:

splitting the light beam, using a beam splitter, into a first portion directed at the bone mass in the patient and a second portion directed at a calibration material;

receiving, from the hybrid MWPM component, at least one calibration measurement associated the second portion of the laser energy; and adjusting the at least one measurement associated with the bone mass based on the at least one calibration measurement before identifying the one or more reference patients.

19. The computer-implemented method of any of examples 17 and 18 wherein the hybrid MWPM component includes a neodymium-doped yttrium aluminum garnet laser.

20. The computer-implemented method of any of examples 17-19 wherein determining the diagnosis includes determining whether a metric in the at least one measurement exceeds a threshold value.

21. The computer-implemented method of example 20 wherein the threshold value is set based on the previous measurements each of the one or more identified reference cases.

22. The computer-implemented method of examples 20 and 21, further comprising retrieving the threshold value from an external database.

23. A computer-implemented method for real-time mapping and analysis of target tissue, the method comprising:

receiving, from a tissue mapping device, patient data of a patient, wherein:
the tissue mapping device includes a hybrid imaging component configured to take two or more wavelength-based measurements of the target tissue, and
the received patient data includes one or more images of the target tissue and at least two or more wavelength-based measurements of the target tissue;

correlating, using a computing system, the two or more wavelength-based measurements to a plurality of stored reference cases;

identifying, using the computing system, one or more reference cases, from the plurality of stored reference cases, based on one or more correlations between the two or more wavelength-based measurements received from the hybrid imaging component and previous measurements in each the plurality of stored reference cases;

determining, using the computing system and based on the one or more identified reference cases, a diagnosis of the target tissue;

generating, using the computing system, a diagnostic map of the target tissue based on the image data and the diagnosis of the target tissue; and sending, using the computing system, the diagnostic map to a computing device accessible by a surgeon.

24. The compute-implemented method of example 23 wherein the patient data is received during a surgical operation on a patient, and wherein the diagnostic map is displayed on the computing device during the surgical operation on the patient.

25. The compute-implemented method of any of examples 23 and 24 wherein the two or more wavelength-based measurements include at least one of an ultrasound image, a multiwavelength photoacoustic measurement, a µ3 measurement, an x-ray image, and a computerized tomography scan.

26. The compute-implemented method of any of examples 23 and 24 wherein the two or more wavelength-based measurements include at least a first x-ray image taken at a first wavelength and a second x-ray image taken at a second wavelength different than the first wavelength.

27. A system for performing real-time analysis of bone tissue during a surgical procedure, the system comprising:
one or more computer processors; and
a non-transitory computer-readable storage medium storing computer instructions, which when executed by the one or more computer processors, cause the system to perform any of the actions of examples 23-26.

CONCLUSION

From the foregoing, it will be appreciated that specific embodiments of the technology have been described herein for purposes of illustration, but well-known structures and functions have not been shown or described in detail to avoid unnecessarily obscuring the description of the embodiments of the technology. To the extent any material incorporated herein by reference conflicts with the present disclosure, the present disclosure controls. Where the context permits, singular or plural terms may also include the plural or singular term, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Furthermore, as used herein, the phrase "and/or" as in "A and/or B" refers to A alone, B alone, and both A and B. Additionally, the terms "comprising," "including," "having," and "with" are used throughout to mean including at least the recited feature(s) such that any greater number of the same features and/or additional types of other features are not precluded. Further, the terms "approximately" and "about" are used herein to mean within at least within 10 percent of a given value or limit. Purely by way of example, an approximate ratio means within a ten percent of the given ratio.

From the foregoing, it will also be appreciated that various modifications may be made without deviating from the disclosure or the technology. For example, one of ordinary skill in the art will understand that various components of the technology can be further divided into subcomponents, or that various components and functions of the technology may be combined and integrated. In addition, certain aspects of the technology described in the context of particular embodiments may also be combined or eliminated in other embodiments.

Furthermore, although advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A computer-implemented method for real-time mapping and analysis of bone tissue, the method comprising:
receiving, from a bone tissue mapper device, patient data of a patient, wherein the bone tissue mapper device includes a hybrid multi-wavelength photoacoustic measurements (MWPM) unit, and wherein the received patient data includes one or more images of at least one target tissue of the bone tissue and at least one measurement of the at least one target tissue from the hybrid MWPM unit;

correlating, using a computing system, the at least one measurement to a plurality of stored reference cases;

identifying, using the computing system, one or more reference cases, from the plurality of stored reference cases, based on one or more correlations between the at least one measurement received from the hybrid MWPM unit and previous measurements in each the plurality of stored reference cases;

determining, using the computing system and based on the one or more identified reference cases, a diagnosis of a bone condition of the at least one target tissue;

generating, using the computing system, a diagnostic map of the bone tissue based on the image data and the diagnosis of the bone condition of the at least one target tissue; and sending, using the computing system, the diagnostic map to a computing device accessible by a surgeon.

2. The method of claim 1, wherein the diagnostic map includes a three-dimensional (3D) bone map of a bone in the at least one target tissue, and wherein the method further comprises:

analyzing the 3D bone map using a machine learning model trained using bone tissue training sets to determine at least one surgical step based on the 3D bone map; and performing, using a robotic surgery system, the at least one surgical step on the patient.

3. The method of claim 1 wherein the at least one measurement includes a measurement of one or more of: bone mineral density, an µ3 value, and a MWPM value.

4. The method of claim 1 wherein each of the plurality of reference cases includes measurements from a related hybrid MWPM component, one or more other measurements related to an associated patient, and diagnostic information for the associated patient.

5. The method of claim 1 wherein the correlations are identified using an artificial intelligence or machine learning (AI/ML) algorithm.

6. The method of claim 1 wherein the at least one measurement is at least one first measurement received at a first time, and wherein the method further comprises:

receiving at least one second measurement of the at least one target tissue from the hybrid MWPM unit at a second time, wherein identifying the one or more reference cases is further based on correlations between the at least one second measurement and previous measurements of the plurality of reference cases.

7. The method of claim 1 wherein the diagnosis of the bone condition includes one or more of: osteoporosis, clinical osteopenia, bone cancer, normal bone with low or high bone mineral density (BMD), and/or osteomyelitis.

8. The method of claim 1 wherein sending the diagnosis of the bone condition to a computing device includes sending an indication of the correlations between the at least one measurement and the previous measurements for review by the surgeon.

9. A system for performing real-time analysis of bone tissue during a surgical procedure, the system comprising:

one or more computer processors; and a non-transitory computer-readable storage medium storing computer instructions, which when executed by the one or more computer processors, cause the system to:

receive at least one first measurement from a hybrid multi-wavelength photoacoustic measurements (MWPM) component, the at least one first measurement indicative of a first bone material density in a tissue sample of a patient;

receive image data of the tissue sample from an imaging device, wherein the imaging device is spatially coupled to the MWPM component;

retrieve a plurality of reference cases, wherein each reference case is associated with an individual reference patient, and wherein each reference case includes at least one second measurement indicative of a second bone material density in a tissue sample of the individual reference patient;

identify one or more reference cases from the plurality of reference cases based on correlations between the at least one first measurement and the at least one second measurement in each reference case;

determine, based on the one or more identified reference cases, at least one diagnosis of a bone condition in the tissue sample of the patient;

generating a diagnostic map of the tissue sample based on the image data and the at least one diagnosis of the bone condition in the tissue sample of the patient; and display, on a user interface accessible by a surgeon before or during a surgical operation on the patient, the diagnostic map.

10. The system of claim 9, further comprising a network interface, wherein the computer instructions further cause the system to retrieve the plurality of reference cases from a third party database via the network interface.

11. The system of claim 9 wherein the diagnostic map includes a three-dimensional (3D) map the tissue sample of the patient based at least in part on the at least one first measurement and the image data.

12. The system of claim 11 wherein the at least one first measurement is two or more first measurements, wherein the 3D map includes two or more selectable layers, and wherein each of the selectable layers is associated with a corresponding one of the two or more measurements.

13. The system of claim 11 wherein the at least one diagnosis of the bone condition is at least two diagnoses of the bone condition, wherein the 3D map includes two or more selectable layers, and wherein each of the selectable layers is associated with an individual one of the at least two diagnoses.

14. The system of claim 11 wherein the 3D map is further based at least in part on the image data from the imaging device.

15. The system of claim 9, wherein the computer instructions further cause the system to:

monitor, through the imaging device, one or more specific aspects of bone tissue in the tissue sample of the patient based on diagnostic information in the one or more identified reference cases.

16. The system of claim 15 wherein the one or more specific aspects of bone tissue include at least one of porous structures and high density structures.

17. A computer-implemented method for performing real-time analysis of bone tissue during a surgical procedure, the computer-implemented method comprising:

receiving, from a hybrid multi-wavelength photoacoustic measurements (MWPM) component, at least one measurement associated with tissue sample of a bone mass in a patient;

receiving, from an imaging device, image data related to the tissue sample, wherein the imaging device is coupled to the hybrid MWPM component to image the tissue sample from a single position;

identifying one or more reference patients from a plurality of reference cases based on correlations between the at least one measurement and previous measurements associated with previous tissue samples of bone mass in each of the plurality of reference cases;

determining, based on the one or more identified reference cases, a diagnosis of at least one bone condition of the patient;

generating a diagnostic map of the tissue sample based on the image data and the diagnosis of the at least one bone condition of the patient; and sending the diagnosis to a computing device accessible by a medical professional.

18. The computer-implemented method of claim 17 wherein the hybrid MWPM component includes a laser device configured to emit a light beam used in performing the at least one measurement, and wherein the method further comprises:

splitting the light beam, using a beam splitter, into a first portion directed at the bone mass in the patient and a second portion directed at a calibration material;

receiving, from the hybrid MWPM component, at least one calibration measurement associated the second portion of the light beam; and adjusting the at least one measurement associated with the bone mass based on the at least one calibration measurement before identifying the one or more reference patients.

19. The computer-implemented method of claim 17 wherein the hybrid MWPM component includes a neodymium-doped yttrium aluminum garnet laser.

20. The computer-implemented method of claim 17 wherein determining the diagnosis includes determining whether a metric in the at least one measurement exceeds a threshold value.

* * * * *